(12) United States Patent  
Brown et al.

(10) Patent No.: US 7,597,715 B2
(45) Date of Patent: Oct. 6, 2009

(54) METHOD AND APPARATUS FOR USE OF POROUS IMPLANTS

(75) Inventors: David R Brown, Warsaw, IN (US); Jason D Meridew, Syracuse, IN (US); Robert M Ronk, Pierceton, IN (US); Troy W Hershberger, Winona Lake, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 46 days.

(21) Appl. No.: 11/357,868

(22) Filed: Feb. 17, 2006

(65) Prior Publication Data

US 2006/0241781 A1    Oct. 26, 2006

Related U.S. Application Data

(63) Continuation-in-part of application No. 11/294,692, filed on Dec. 5, 2005, which is a continuation-in-part of application No. 11/111,123, filed on Apr. 21, 2005.

(51) Int. Cl.
*A61F 2/32* (2006.01)

(52) U.S. Cl. ............... 623/22.32; 623/22.24; 623/22.29; 623/22.43; 623/23.55; 623/22.12

(58) Field of Classification Search .............. 623/22.21, 623/22.24, 22.33, 22.34, 22.37, 22.38, 23.53, 623/23.55

See application file for complete search history.

(56) References Cited

U.S. PATENT DOCUMENTS

| 3,353,259 A | 11/1967 | Kirkpatrick |
| 3,605,123 A | 9/1971 | Hahn |

(Continued)

FOREIGN PATENT DOCUMENTS

DE    24 04 214 C3    1/1974

(Continued)

OTHER PUBLICATIONS

Bram, Martin, et al., High-Porosity Titanium, Stainless Steel, and Superalloy Parts, Advanced Engineering Materials 2000, 2, No. 4, 196-199.

(Continued)

*Primary Examiner*—David H Willse
*Assistant Examiner*—Javier G Blanco
(74) *Attorney, Agent, or Firm*—Harness, Dickey

(57) ABSTRACT

An orthopedic prosthesis for implantation into a bone of a patient includes a porous metal shell adapted to be affixed within the bone. The porous metal shell includes an outer surface adapted to receive bone ingrowth and an inner surface adapted to engage a liner. The porous metal shell is porous from the outer surface to the inner surface. A non-porous member may be affixed to the porous metal shell. The non-porous member may include a piercing member extending from the outer surface, the piercing member adapted to penetrate the bone in an implanted position. The non-porous member may include spikes or fins. In one example, the piercing member may define a reduced material cross section at an interface with the outer surface of the porous metal shell. The piercing member may be adapted to be broken at the reduced material cross section and removed from the porous metal shell.

17 Claims, 20 Drawing Sheets

U.S. PATENT DOCUMENTS

| | | | |
|---|---|---|---|
| 3,677,795 A | 7/1972 | Bokros et al. |
| 3,808,606 A | 5/1974 | Tronzo |
| 3,840,904 A | 10/1974 | Tronzo |
| 3,855,638 A | 12/1974 | Pilliar |
| 3,896,500 A | 7/1975 | Rambert et al. |
| 3,905,777 A | 9/1975 | Lacroix |
| 3,906,550 A | 9/1975 | Rostoker et al. |
| 3,938,499 A | 2/1976 | Bucalo |
| 3,986,212 A | 10/1976 | Sauer |
| 4,051,559 A | 10/1977 | Pifferi |
| 4,164,794 A | 8/1979 | Spector et al. |
| 4,168,326 A | 9/1979 | Broemer et al. |
| 4,184,213 A | 1/1980 | Heimke |
| 4,187,559 A | 2/1980 | Grell et al. |
| 4,205,400 A | 6/1980 | Shen et al. |
| 4,206,271 A | 6/1980 | Norling et al. |
| 4,217,666 A | 8/1980 | Averill |
| 4,224,698 A | 9/1980 | Hopson |
| 4,234,972 A | 11/1980 | Hench et al. |
| 4,285,070 A | 8/1981 | Averill |
| 4,307,472 A | 12/1981 | Morris |
| 4,309,488 A | 1/1982 | Heide et al. |
| 4,330,891 A | 5/1982 | Brånemark et al. |
| 4,345,339 A | 8/1982 | Müller et al. |
| 4,351,069 A | 9/1982 | Ballintyn et al. |
| 4,355,428 A | 10/1982 | Deloison et al. |
| 4,362,681 A | 12/1982 | Spector et al. |
| 4,479,271 A | 10/1984 | Bolesky et al. |
| 4,542,539 A | 9/1985 | Rowe, Jr. et al. |
| 4,563,778 A | 1/1986 | Roche et al. |
| 4,566,138 A | 1/1986 | Lewis et al. |
| 4,570,271 A | 2/1986 | Sump |
| 4,612,160 A | 9/1986 | Donlevy et al. |
| 4,636,219 A | 1/1987 | Pratt et al. |
| 4,644,942 A | 2/1987 | Sump |
| 4,659,331 A | 4/1987 | Matthews et al. |
| 4,666,450 A | 5/1987 | Kenna |
| 4,685,923 A | 8/1987 | Mathys |
| 4,693,721 A | 9/1987 | Ducheyne |
| 4,715,859 A | 12/1987 | Schelhas et al. |
| 4,715,860 A | 12/1987 | Amstutz et al. |
| 4,743,256 A | 5/1988 | Brantigan |
| 4,743,262 A | 5/1988 | Tronzo |
| 4,756,862 A | 7/1988 | Spector et al. |
| 4,769,041 A | 9/1988 | Morscher |
| 4,778,473 A | 10/1988 | Matthews et al. |
| 4,778,474 A | 10/1988 | Homsy |
| 4,795,469 A | 1/1989 | Oh |
| 4,801,301 A | 1/1989 | Noiles |
| 4,813,959 A | 3/1989 | Cremascoli |
| 4,840,632 A | 6/1989 | Kampner |
| 4,842,606 A | 6/1989 | Kranz et al. |
| 4,851,006 A | 7/1989 | Tuke |
| 4,854,496 A | 8/1989 | Bugle |
| 4,863,474 A | 9/1989 | Brown et al. |
| 4,863,475 A | 9/1989 | Andersen et al. |
| 4,863,538 A | 9/1989 | Deckard |
| 4,871,368 A * | 10/1989 | Wagner .................. 623/22.29 |
| 4,883,490 A | 11/1989 | Oh |
| 4,883,491 A | 11/1989 | Mallory et al. |
| 4,892,549 A | 1/1990 | Figgie, III et al. |
| 4,904,265 A | 2/1990 | MacCollum et al. |
| 4,919,675 A * | 4/1990 | Dietschi .................. 623/22.26 |
| 4,923,473 A | 5/1990 | Griss et al. |
| 4,936,847 A | 6/1990 | Manginelli |
| 4,936,856 A | 6/1990 | Keller et al. |
| 4,936,861 A | 6/1990 | Muller et al. |
| 4,944,759 A | 7/1990 | Mallory et al. |
| 4,950,270 A | 8/1990 | Bowman et al. |
| 4,950,299 A | 8/1990 | Noiles |
| 4,955,919 A | 9/1990 | Pappas et al. |
| 4,957,819 A | 9/1990 | Kawahara et al. |
| 4,963,154 A | 10/1990 | Anapliotis et al. |
| 4,969,907 A | 11/1990 | Koch et al. |
| 4,969,910 A | 11/1990 | Frey et al. |
| 4,976,738 A | 12/1990 | Frey et al. |
| 4,978,355 A | 12/1990 | Frey et al. |
| 4,978,356 A | 12/1990 | Noiles |
| 4,978,358 A | 12/1990 | Bobyn |
| 4,997,445 A | 3/1991 | Hodorek |
| 5,004,476 A | 4/1991 | Cook |
| 5,009,665 A | 4/1991 | Serbousek et al. |
| 5,013,324 A | 5/1991 | Zolman et al. |
| 5,018,285 A | 5/1991 | Zolman et al. |
| 5,019,105 A | 5/1991 | Wiley |
| 5,021,062 A | 6/1991 | Adrey et al. |
| 5,021,063 A | 6/1991 | Täger |
| 5,024,670 A | 6/1991 | Smith et al. |
| 5,027,998 A | 7/1991 | Bugle |
| 5,030,233 A | 7/1991 | Ducheyne |
| 5,047,182 A | 9/1991 | Sundback et al. |
| 5,080,672 A | 1/1992 | Bellis |
| 5,080,674 A | 1/1992 | Jacobs et al. |
| 5,080,685 A | 1/1992 | Bolesky et al. |
| 5,084,051 A | 1/1992 | Tormala et al. |
| 5,092,897 A | 3/1992 | Forte |
| 5,096,518 A | 3/1992 | Fujikawa et al. |
| 5,098,435 A | 3/1992 | Stednitz et al. |
| 5,104,410 A | 4/1992 | Chowdhary |
| 5,108,432 A | 4/1992 | Gustavson |
| 5,133,764 A | 7/1992 | Pappas et al. |
| 5,152,796 A | 10/1992 | Slamin |
| 5,152,797 A | 10/1992 | Luckman et al. |
| 5,156,626 A | 10/1992 | Broderick et al. |
| 5,163,961 A | 11/1992 | Harwin |
| 5,167,502 A | 12/1992 | Kawahara et al. |
| 5,176,711 A | 1/1993 | Grimes |
| 5,181,928 A | 1/1993 | Bolesky et al. |
| 5,192,329 A | 3/1993 | Christie et al. |
| 5,198,308 A | 3/1993 | Shetty et al. |
| 5,201,766 A | 4/1993 | Georgette |
| 5,203,787 A | 4/1993 | Noblitt et al. |
| 5,211,665 A | 5/1993 | Ku |
| 5,226,915 A | 7/1993 | Bertin |
| 5,236,457 A | 8/1993 | Devanathan |
| 5,236,462 A | 8/1993 | Mikhail |
| 5,246,530 A | 9/1993 | Bugle et al. |
| 5,282,861 A | 2/1994 | Kaplan |
| 5,286,260 A | 2/1994 | Bolesky et al. |
| 5,290,315 A | 3/1994 | DeCarlo, Jr. |
| 5,310,408 A | 5/1994 | Schryver et al. |
| 5,314,490 A | 5/1994 | Wagner et al. |
| 5,323,954 A | 6/1994 | Shetty et al. |
| 5,326,367 A | 7/1994 | Robioneck |
| 5,326,368 A | 7/1994 | Collazo |
| 5,343,877 A | 9/1994 | Park |
| 5,348,788 A | 9/1994 | White |
| 5,358,532 A | 10/1994 | Evans et al. |
| 5,360,448 A | 11/1994 | Thramann |
| 5,360,452 A | 11/1994 | Engelhardt et al. |
| 5,370,692 A | 12/1994 | Fink et al. |
| 5,370,698 A | 12/1994 | Heimke et al. |
| 5,370,702 A | 12/1994 | Jones |
| 5,370,704 A | 12/1994 | DeCarlo, Jr. |
| 5,370,706 A | 12/1994 | Bolesky et al. |
| 5,376,122 A | 12/1994 | Pappas et al. |
| 5,380,325 A | 1/1995 | Lahille et al. |
| 5,397,359 A | 3/1995 | Mittelmeier et al. |
| 5,405,389 A | 4/1995 | Conta et al. |
| 5,415,704 A | 5/1995 | Davidson |
| 5,443,510 A | 8/1995 | Shetty et al. |
| 5,443,512 A | 8/1995 | Parr et al. |
| 5,443,519 A | 8/1995 | Averill et al. |
| 5,484,539 A | 1/1996 | Tersi et al. |

| Patent No. | Date | Inventor |
|---|---|---|
| 5,486,181 A | 1/1996 | Cohen et al. |
| 5,496,372 A | 3/1996 | Hamamoto et al. |
| 5,504,300 A | 4/1996 | Devanathan et al. |
| 5,505,984 A | 4/1996 | England et al. |
| 5,509,933 A | 4/1996 | Davidson et al. |
| 5,534,027 A | 7/1996 | Hodorek |
| 5,535,810 A | 7/1996 | Compton et al. |
| 5,540,713 A | 7/1996 | Schnepp-Pesch et al. |
| 5,545,227 A | 8/1996 | Davidson et al. |
| 5,549,685 A | 8/1996 | Hayes |
| 5,549,691 A | 8/1996 | Harwin |
| 5,549,698 A | 8/1996 | Averill et al. |
| 5,549,701 A | 8/1996 | Mikhail |
| 5,571,187 A | 11/1996 | Devanathan |
| 5,571,194 A | 11/1996 | Gabriel |
| 5,571,198 A | 11/1996 | Drucker et al. |
| 5,571,200 A | 11/1996 | Cohen et al. |
| 5,571,201 A | 11/1996 | Averill et al. |
| 5,573,401 A | 11/1996 | Davidson et al. |
| 5,593,451 A | 1/1997 | Averill et al. |
| 5,609,641 A | 3/1997 | Johnson et al. |
| 5,609,645 A | 3/1997 | Vinciguerra |
| 5,609,646 A | 3/1997 | Field et al. |
| 5,639,280 A | 6/1997 | Warner et al. |
| 5,658,338 A | 8/1997 | Tullos et al. |
| 5,658,347 A | 8/1997 | Sarkisian et al. |
| 5,658,348 A | 8/1997 | Rohr, Jr. |
| 5,665,119 A | 9/1997 | Koller |
| 5,676,700 A | 10/1997 | Black et al. |
| 5,676,704 A | 10/1997 | Ries et al. |
| 5,688,453 A | 11/1997 | England et al. |
| 5,702,473 A | 12/1997 | Albrektsson et al. |
| 5,702,477 A | 12/1997 | Capello et al. |
| 5,702,483 A | 12/1997 | Kwong |
| 5,702,487 A | 12/1997 | Averill et al. |
| 5,723,011 A | 3/1998 | Devanathan et al. |
| 5,723,014 A | 3/1998 | Laurent et al. |
| 5,725,587 A | 3/1998 | Garber |
| 5,728,510 A | 3/1998 | White |
| 5,734,959 A | 3/1998 | Krebs et al. |
| 5,755,743 A | 5/1998 | Volz et al. |
| 5,755,806 A | 5/1998 | Stalcup et al. |
| 5,782,928 A | 7/1998 | Ries et al. |
| 5,782,929 A | 7/1998 | Sederholm |
| 5,798,308 A | 8/1998 | Chatterjee et al. |
| 5,824,107 A | 10/1998 | Tschirren |
| 5,824,108 A | 10/1998 | Huebner |
| 5,863,295 A | 1/1999 | Averill et al. |
| 5,871,548 A | 2/1999 | Sanders et al. |
| 5,879,398 A | 3/1999 | Swarts et al. |
| 5,879,399 A | 3/1999 | Church |
| 5,879,401 A | 3/1999 | Besemer et al. |
| 5,879,404 A | 3/1999 | Bateman et al. |
| 5,879,405 A | 3/1999 | Ries et al. |
| 5,888,205 A | 3/1999 | Pratt et al. |
| 5,904,720 A | 5/1999 | Farrar et al. |
| 5,916,268 A | 6/1999 | Schollner et al. |
| 5,925,077 A * | 7/1999 | Williamson et al. ...... 623/22.34 |
| 5,926,685 A | 7/1999 | Krebs et al. |
| 5,931,870 A | 8/1999 | Cuckler et al. |
| 5,938,702 A | 8/1999 | Lopez et al. |
| 5,972,032 A | 10/1999 | Lopez et al. |
| 5,976,148 A | 11/1999 | Charpenet et al. |
| 5,981,828 A | 11/1999 | Nelson et al. |
| 5,989,293 A | 11/1999 | Cook et al. |
| 6,008,432 A | 12/1999 | Taylor |
| 6,013,104 A | 1/2000 | Kampner |
| 6,022,509 A | 2/2000 | Matthews et al. |
| 6,042,611 A | 3/2000 | Noiles |
| 6,042,612 A | 3/2000 | Voydeville |
| 6,049,054 A | 4/2000 | Panchison et al. |
| 6,063,442 A | 5/2000 | Cohen et al. |
| 6,066,176 A | 5/2000 | Oshida |
| 6,087,553 A | 7/2000 | Cohen et al. |
| 6,099,529 A | 8/2000 | Gertzman et al. |
| 6,129,765 A | 10/2000 | Lopez et al. |
| 6,132,469 A | 10/2000 | Schroeder |
| 6,132,674 A | 10/2000 | Compton et al. |
| 6,136,029 A | 10/2000 | Johnson et al. |
| 6,139,574 A | 10/2000 | Vacanti et al. |
| 6,143,036 A | 11/2000 | Comfort |
| 6,143,293 A | 11/2000 | Weiss et al. |
| 6,149,689 A | 11/2000 | Grundei |
| 6,152,962 A | 11/2000 | DeCarlo, Jr. |
| 6,162,257 A | 12/2000 | Gustilo et al. |
| 6,165,222 A | 12/2000 | Hoeppner et al. |
| 6,176,879 B1 | 1/2001 | Reischl et al. |
| 6,187,050 B1 | 2/2001 | Khalili et al. |
| 6,192,272 B1 | 2/2001 | Fiedler |
| 6,193,761 B1 | 2/2001 | Treacy |
| 6,197,065 B1 | 3/2001 | Martin et al. |
| 6,203,844 B1 | 3/2001 | Park |
| 6,206,924 B1 | 3/2001 | Timm |
| 6,217,620 B1 | 4/2001 | Park |
| 6,228,121 B1 | 5/2001 | Khalili |
| 6,231,612 B1 | 5/2001 | Balay et al. |
| 6,240,616 B1 | 6/2001 | Yan |
| 6,253,443 B1 | 7/2001 | Johnson |
| 6,273,891 B1 | 8/2001 | Masini |
| 6,290,726 B1 | 9/2001 | Pope et al. |
| 6,293,971 B1 | 9/2001 | Nelson et al. |
| 6,296,667 B1 | 10/2001 | Johnson et al. |
| 6,302,913 B1 | 10/2001 | Ripamonti et al. |
| 6,306,173 B1 | 10/2001 | Masini |
| 6,309,546 B1 | 10/2001 | Herrmann et al. |
| 6,322,728 B1 | 11/2001 | Brodkin et al. |
| 6,340,370 B1 | 1/2002 | Willert et al. |
| 6,352,559 B1 | 3/2002 | Church |
| 6,365,092 B1 | 4/2002 | Backa et al. |
| 6,376,573 B1 | 4/2002 | White et al. |
| 6,391,251 B1 | 5/2002 | Keicher et al. |
| 6,416,553 B1 | 7/2002 | White et al. |
| 6,432,142 B1 | 8/2002 | Kamiya et al. |
| 6,443,991 B1 | 9/2002 | Running |
| 6,447,543 B1 | 9/2002 | Studer et al. |
| 6,447,550 B1 | 9/2002 | Hunter et al. |
| 6,454,811 B1 | 9/2002 | Sherwood et al. |
| 6,458,161 B1 | 10/2002 | Gibbs et al. |
| 6,461,385 B1 | 10/2002 | Gayer et al. |
| 6,475,243 B1 | 11/2002 | Sheldon et al. |
| 6,497,727 B1 | 12/2002 | Pope et al. |
| 6,506,192 B1 | 1/2003 | Gertzman et al. |
| 6,508,841 B2 | 1/2003 | Martin et al. |
| 6,520,995 B2 | 2/2003 | Church |
| 6,527,774 B2 | 3/2003 | Lieberman |
| 6,527,807 B1 | 3/2003 | O'Neil et al. |
| 6,530,958 B1 | 3/2003 | Cima et al. |
| 6,537,321 B1 | 3/2003 | Horber |
| 6,558,428 B2 | 5/2003 | Park |
| 6,572,655 B2 | 6/2003 | Johnson |
| 6,585,772 B2 | 7/2003 | Hunter et al. |
| 6,592,622 B1 | 7/2003 | Ferguson |
| 6,605,293 B1 | 8/2003 | Giordano et al. |
| 6,605,648 B1 | 8/2003 | Johnson et al. |
| 6,610,097 B2 | 8/2003 | Serbousek et al. |
| 6,613,093 B2 | 9/2003 | DeCarlo, Jr. et al. |
| 6,620,200 B1 | 9/2003 | Descamps et al. |
| 6,621,039 B2 | 9/2003 | Wang et al. |
| 6,626,947 B2 | 9/2003 | Lester et al. |
| 6,626,950 B2 | 9/2003 | Brown et al. |
| 6,641,616 B1 | 11/2003 | Grundei |
| 6,645,206 B1 | 11/2003 | Zdeblick et al. |
| 6,652,586 B2 | 11/2003 | Hunter et al. |
| 6,660,040 B2 | 12/2003 | Chan et al. |
| 6,660,224 B2 | 12/2003 | Lefebvre et al. |
| RE38,409 E | 1/2004 | Noiles |

| | | | | | | |
|---|---|---|---|---|---|---|
| 6,676,704 B1 | 1/2004 | Pope et al. | | 2004/0083004 A1 | 4/2004 | Wasielewski |
| 6,676,892 B2 | 1/2004 | Das et al. | | 2004/0088038 A1 | 5/2004 | Dehnad et al. |
| 6,682,566 B2 | 1/2004 | Draenert | | 2004/0098127 A1 | 5/2004 | Charlebois et al. |
| 6,682,567 B1 | 1/2004 | Schroeder | | 2004/0102854 A1 | 5/2004 | Zhu |
| 6,686,437 B2 | 2/2004 | Buchman et al. | | 2004/0109853 A1 | 6/2004 | McDaniel |
| 6,695,884 B1 | 2/2004 | Townley | | 2004/0122521 A1 | 6/2004 | Lee et al. |
| 6,696,073 B2 | 2/2004 | Boyce et al. | | 2004/0126265 A1 | 7/2004 | Takiguchi |
| 6,709,462 B2 | 3/2004 | Hanssen | | 2004/0126583 A1 | 7/2004 | Nakamura et al. |
| 6,725,901 B1 | 4/2004 | Kramer et al. | | 2004/0137218 A1 | 7/2004 | Liu et al. |
| 6,726,723 B2 | 4/2004 | Running | | 2004/0166340 A1 | 8/2004 | Cairns et al. |
| 6,726,725 B2 | 4/2004 | Hunter et al. | | 2004/0172137 A1 | 9/2004 | Blaylock et al. |
| 6,758,864 B2 | 7/2004 | Storer et al. | | 2004/0186553 A1 | 9/2004 | Yan |
| 6,770,099 B2 | 8/2004 | Andriacchi et al. | | 2004/0199258 A1 | 10/2004 | Macara |
| 6,783,551 B1 | 8/2004 | Metzger et al. | | 2004/0199260 A1 | 10/2004 | Pope et al. |
| 6,800,094 B2 | 10/2004 | Burkinshaw | | 2004/0210316 A1 | 10/2004 | King et al. |
| 6,811,569 B1 | 11/2004 | Afriat et al. | | 2004/0225369 A1 | 11/2004 | Lakin et al. |
| 6,827,742 B2 | 12/2004 | Hayes, Jr. et al. | | 2004/0225371 A1 | 11/2004 | Roger |
| 6,840,960 B2 | 1/2005 | Bubb | | 2004/0229029 A1 | 11/2004 | Bowles et al. |
| 6,866,685 B2 | 3/2005 | Chan et al. | | 2004/0238410 A1 | 12/2004 | Inoue et al. |
| 6,869,447 B2 | 3/2005 | Lee et al. | | 2004/0243133 A1 | 12/2004 | Materna |
| 6,896,703 B2 | 5/2005 | Barbieri et al. | | 2005/0004677 A1 | 1/2005 | Johnson |
| 6,908,486 B2 | 6/2005 | Lewallen | | 2005/0004678 A1* | 1/2005 | Richards ................. 623/22.28 |
| 6,916,342 B2 | 7/2005 | Frederick et al. | | 2005/0004680 A1 | 1/2005 | Saladino et al. |
| 6,923,833 B2 | 8/2005 | Wasielewski | | 2005/0010303 A1 | 1/2005 | Nogier |
| 6,926,740 B2 | 8/2005 | Lewis et al. | | 2005/0025656 A1 | 2/2005 | Bhaduri et al. |
| 6,945,448 B2 | 9/2005 | Medlin et al. | | 2005/0031704 A1 | 2/2005 | Ahn |
| 6,981,991 B2 | 1/2006 | Ferree | | 2005/0032025 A1 | 2/2005 | Bhaduri et al. |
| 7,141,073 B2 | 11/2006 | May et al. | | 2005/0035052 A1 | 2/2005 | Kelly et al. |
| 7,156,880 B2 | 1/2007 | Evans et al. | | 2005/0048193 A1 | 3/2005 | Li et al. |
| 7,166,133 B2 | 1/2007 | Evans et al. | | 2005/0049713 A1 | 3/2005 | Garber et al. |
| 7,189,263 B2 | 3/2007 | Erbe et al. | | 2005/0060040 A1 | 3/2005 | Auxepaules et al. |
| 7,192,448 B2 | 3/2007 | Ferree | | 2005/0065307 A1 | 3/2005 | King et al. |
| 2001/0011190 A1 | 8/2001 | Park | | 2005/0065604 A1 | 3/2005 | Stoll |
| 2001/0013166 A1 | 8/2001 | Yan | | 2005/0071015 A1 | 3/2005 | Sekel |
| 2001/0030035 A1 | 10/2001 | Oda | | 2005/0085820 A1 | 4/2005 | Collins et al. |
| 2002/0016635 A1 | 2/2002 | Despres, III et al. | | 2005/0085915 A1 | 4/2005 | Steinberg |
| 2002/0040245 A1 | 4/2002 | Lester et al. | | 2005/0087915 A1 | 4/2005 | Pope et al. |
| 2002/0062154 A1 | 5/2002 | Ayers | | 2005/0090905 A1 | 4/2005 | Hawkins et al. |
| 2002/0068980 A1 | 6/2002 | Serbousek et al. | | 2005/0100470 A1 | 5/2005 | Lefebvre et al. |
| 2002/0123750 A1 | 9/2002 | Eisermann et al. | | 2005/0107883 A1 | 5/2005 | Goodfried et al. |
| 2002/0139504 A1 | 10/2002 | Klein | | 2005/0145364 A1 | 7/2005 | Nakajima |
| 2002/0143403 A1 | 10/2002 | Vaidyanathan et al. | | 2005/0171614 A1 | 8/2005 | Bacon |
| 2002/0151983 A1 | 10/2002 | Shetty | | 2005/0184134 A1 | 8/2005 | Charlebois et al. |
| 2002/0197178 A1 | 12/2002 | Yan | | 2005/0234559 A1 | 10/2005 | Fernandez et al. |
| 2003/0001282 A1 | 1/2003 | Meynen et al. | | 2005/0246032 A1 | 11/2005 | Bokros et al. |
| 2003/0013989 A1 | 1/2003 | Obermiller et al. | | 2006/0002810 A1 | 1/2006 | Grohowski |
| 2003/0033020 A1 | 2/2003 | Hunter et al. | | 2006/0003179 A1 | 1/2006 | Wang et al. |
| 2003/0049299 A1 | 3/2003 | Malaviya et al. | | 2006/0018942 A1 | 1/2006 | Rowe et al. |
| 2003/0050703 A1* | 3/2003 | Harris et al. ................. 623/22.2 | | 2006/0241776 A1 | 10/2006 | Brown et al. |
| 2003/0050705 A1 | 3/2003 | Cueille et al. | | 2006/0241781 A1 | 10/2006 | Brown et al. |
| 2003/0069639 A1 | 4/2003 | Sander et al. | | 2007/0021838 A1 | 1/2007 | Dugas et al. |
| 2003/0083741 A1 | 5/2003 | Woo et al. | | 2007/0129809 A1 | 6/2007 | Meridew et al. |
| 2003/0105529 A1 | 6/2003 | Synder et al. | | 2007/0173948 A1 | 7/2007 | Meridew et al. |
| 2003/0111752 A1 | 6/2003 | Wood et al. | | 2007/0196230 A1 | 8/2007 | Hamman et al. |
| 2003/0114936 A1 | 6/2003 | Sherwood et al. | | 2007/0250175 A1 | 10/2007 | Meridew et al. |
| 2003/0135281 A1 | 7/2003 | Hanssen | | 2007/0264152 A1 | 11/2007 | Zhao |
| 2003/0144741 A1 | 7/2003 | King et al. | | 2008/0147187 A1 | 6/2008 | Bollinger et al. |
| 2003/0144742 A1 | 7/2003 | King et al. | | | | |
| 2003/0153203 A1 | 8/2003 | Nycz et al. | | FOREIGN PATENT DOCUMENTS | | |
| 2003/0153981 A1 | 8/2003 | Wang et al. | | | | |
| 2003/0153982 A1 | 8/2003 | Pria | | DE | 3130732 | 5/1983 |
| 2003/0155686 A1 | 8/2003 | Hawkins et al. | | DE | 3205526 | 9/1983 |
| 2003/0163202 A1 | 8/2003 | Lakin | | DE | 41 33 433 | 5/1993 |
| 2003/0163203 A1 | 8/2003 | Nycz et al. | | DE | 19726961 | 11/1998 |
| 2003/0171818 A1 | 9/2003 | Lewallen | | EP | 0 214 885 | 7/1986 |
| 2003/0200837 A1 | 10/2003 | Matsuura et al. | | EP | 0214885 | 3/1987 |
| 2003/0220696 A1 | 11/2003 | Levine et al. | | EP | 0 378 928 | 7/1990 |
| 2003/0232124 A1 | 12/2003 | Medlin et al. | | EP | 0 538 987 | 4/1993 |
| 2003/0236573 A1 | 12/2003 | Evans et al. | | EP | 0551794 | 7/1993 |
| 2004/0054418 A1 | 3/2004 | McLean et al. | | EP | 0612509 | 8/1994 |
| 2004/0054421 A1 | 3/2004 | McLean | | EP | 0648478 | 4/1995 |
| 2004/0064192 A1 | 4/2004 | Bubb | | EP | 0 807 426 | 11/1997 |
| 2004/0072010 A1 | 4/2004 | Date et al. | | EP | 0 985 386 | 3/2000 |

| | | |
|---|---|---|
| EP | 1082949 | 3/2001 |
| EP | 1 236 450 | 9/2002 |
| EP | 0 806 921 | 1/2003 |
| EP | 1 384 456 | 1/2004 |
| EP | 1421918 | 5/2004 |
| EP | 1 430 856 | 6/2004 |
| FR | 2 148 322 | 3/1973 |
| FR | 2775586 | 9/1999 |
| GB | 2001247 | 1/1979 |
| WO | WO 92/18069 | 4/1992 |
| WO | WO 96/23459 | 1/1996 |
| WO | WO 96/13233 | 5/1996 |
| WO | WO 00/38598 | 7/2000 |
| WO | WO-01/70141 | 9/2001 |
| WO | WO 02/07652 | 1/2002 |
| WO | WO-2004069107 | 8/2004 |
| WO | WO 2004/080340 | 9/2004 |
| WO | WO-2006007861 | 1/2006 |

OTHER PUBLICATIONS

Oliveira, M. V., et al., Porous Structure Characterization in Titanium Coating for Surgical Implants, © 2002, Materials Research, vol. 5, No. 3, 269-273.

Wen, C. E., et al., Novel titanium foam for bone tissue engineering, J. Mater. Res., vol. 17, No. 10, Oct. 2002, 2633-2639.

Wen, C. E., et al., Processing and mechanical properties of autogenous titanium implant materials, Journal of Materials Science: Materials in Medicine 13 (2002), 397-401.

Wen, C. E., Processing of biocompatible porous Ti and Mg, Scripta Materialia 45 (2001) 1147-1153.

Wheeler, K. R., et al., Porous Metals as a Hard Tissue Substitute. Part II. Porous Metal Properties, Biomat., Med. Dev., Art. Org., 1(2), 337-348 (1973).

"Magnum™ large metal articulation, Surgical Technique" brochure, Biomet Orthopedics, Inc., 2004 (12 pages).

International Search Report and Written Opinion for PCT/US2007/03811 mailed Sep. 27, 2007.

Michael S. Bradford, M.D. and Wayne G. Paprosky, M.D., F.A.C.S., Total Accetabular Transplant Allograft Reconstruction of the Severely Deficient Acetabulum, Sunrise Hospital and Medical Center, Las Vegas, NV and Rush-Presbyterian-St. Lukes Medical Center, Chicago, IL, 1995 by W.B. Saunders Company, pp. 1-15.

International Search Report and Written Opinion for PCT/US2008/002372 mailed Dec. 9, 2008 claiming benefit of U.S. Appl. No. 11/709,549, which claims benefit of U.S. Appl. No. 11/546,500, which claims benefit of U.S. Appl. No. 11/357,868, which claims benefit of U.S. Appl. No. 11/294,692, which claims benefit of U.S. Appl. No. 11/111,123.

International Search Report and Written Opinion for PCT/US2008/002372 mailed Jul. 30, 2008 claiming benefit of U.S. Appl. No. 11/709,549, which claims benefit of U.S. Appl. No. 11/546,500, which claims benefit of U.S. Appl. No. 11/357,868, which claims benefit of U.S. Appl. No. 11/294,692, which claims benefit of U.S. Appl. No. 11/111,123.

* cited by examiner

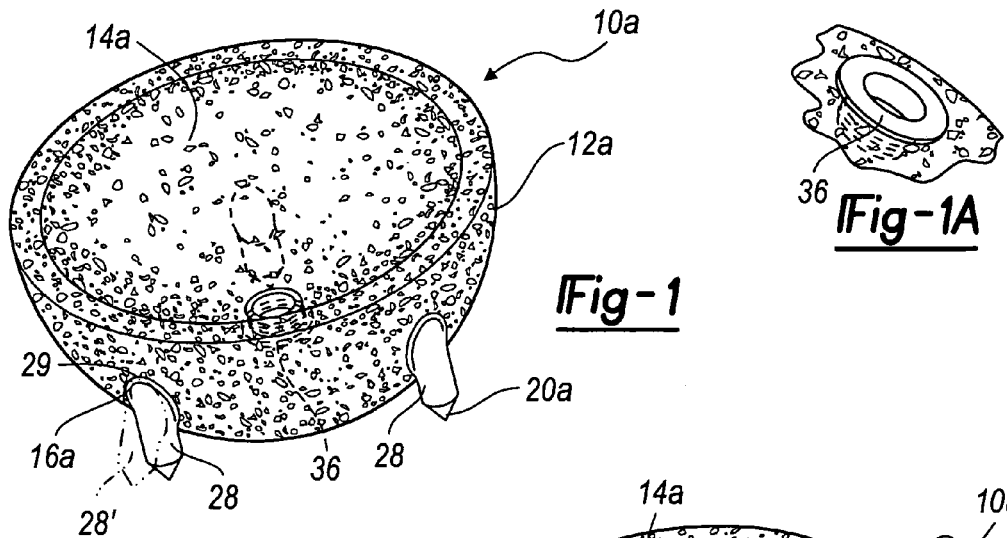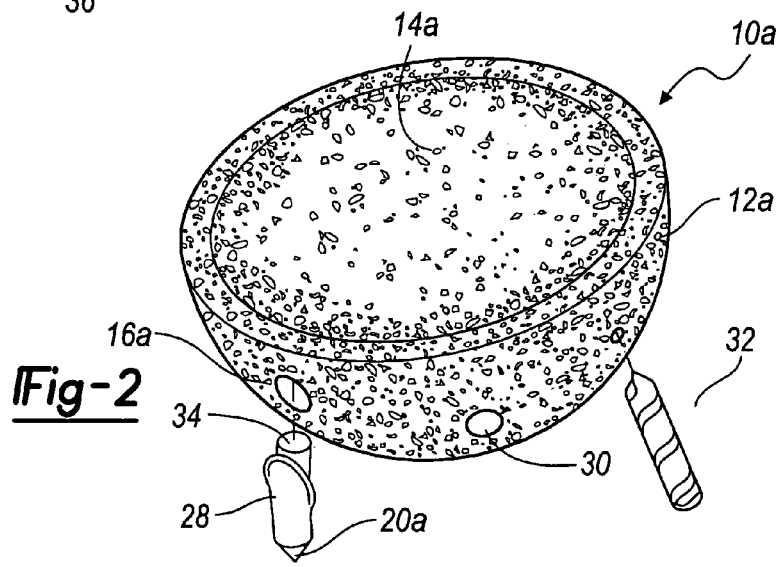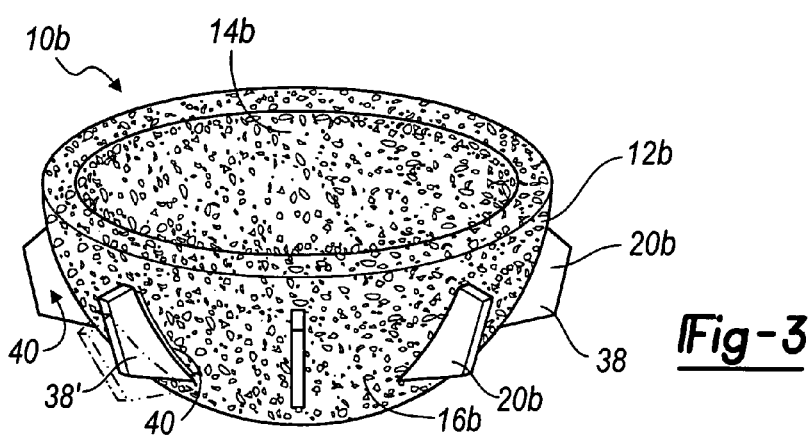

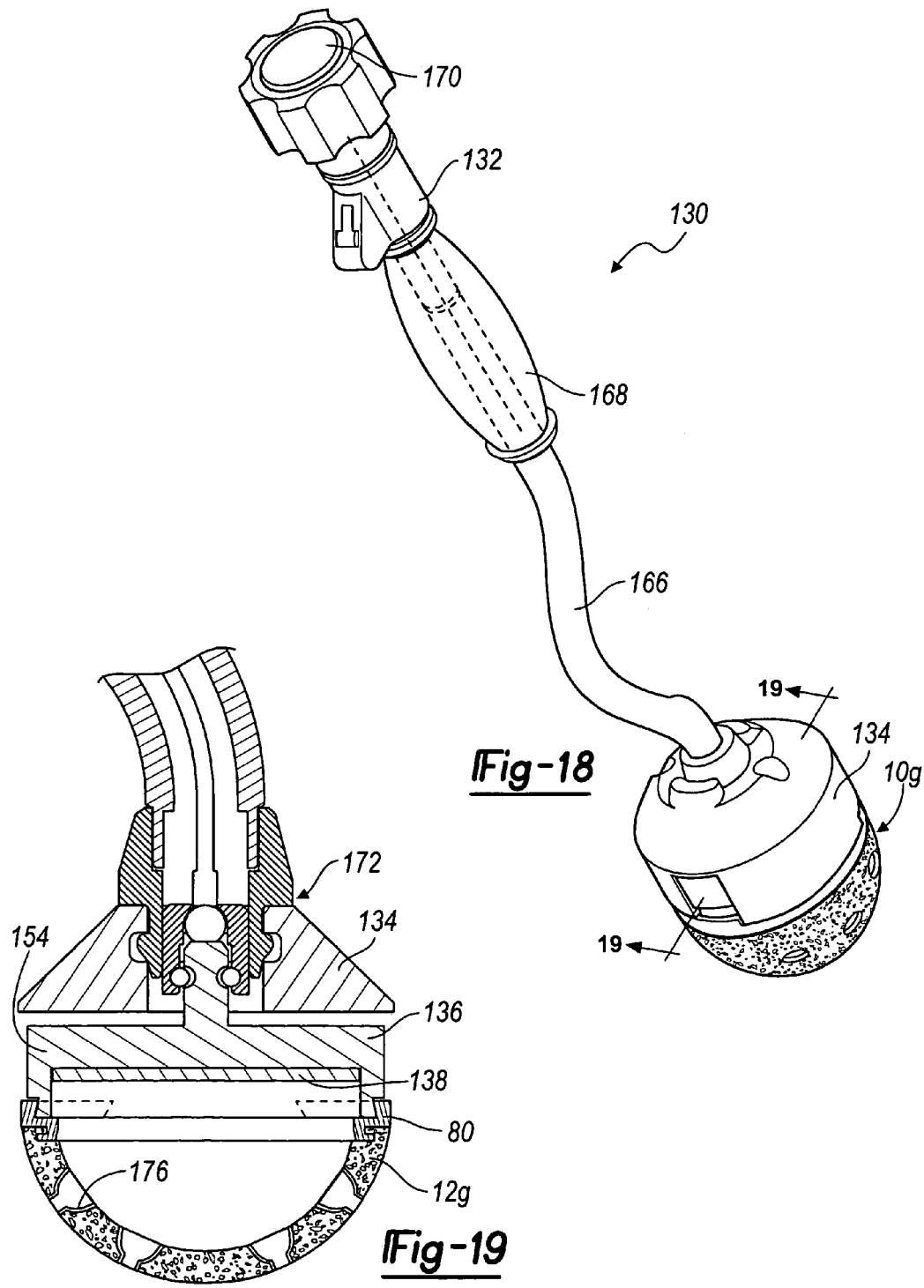

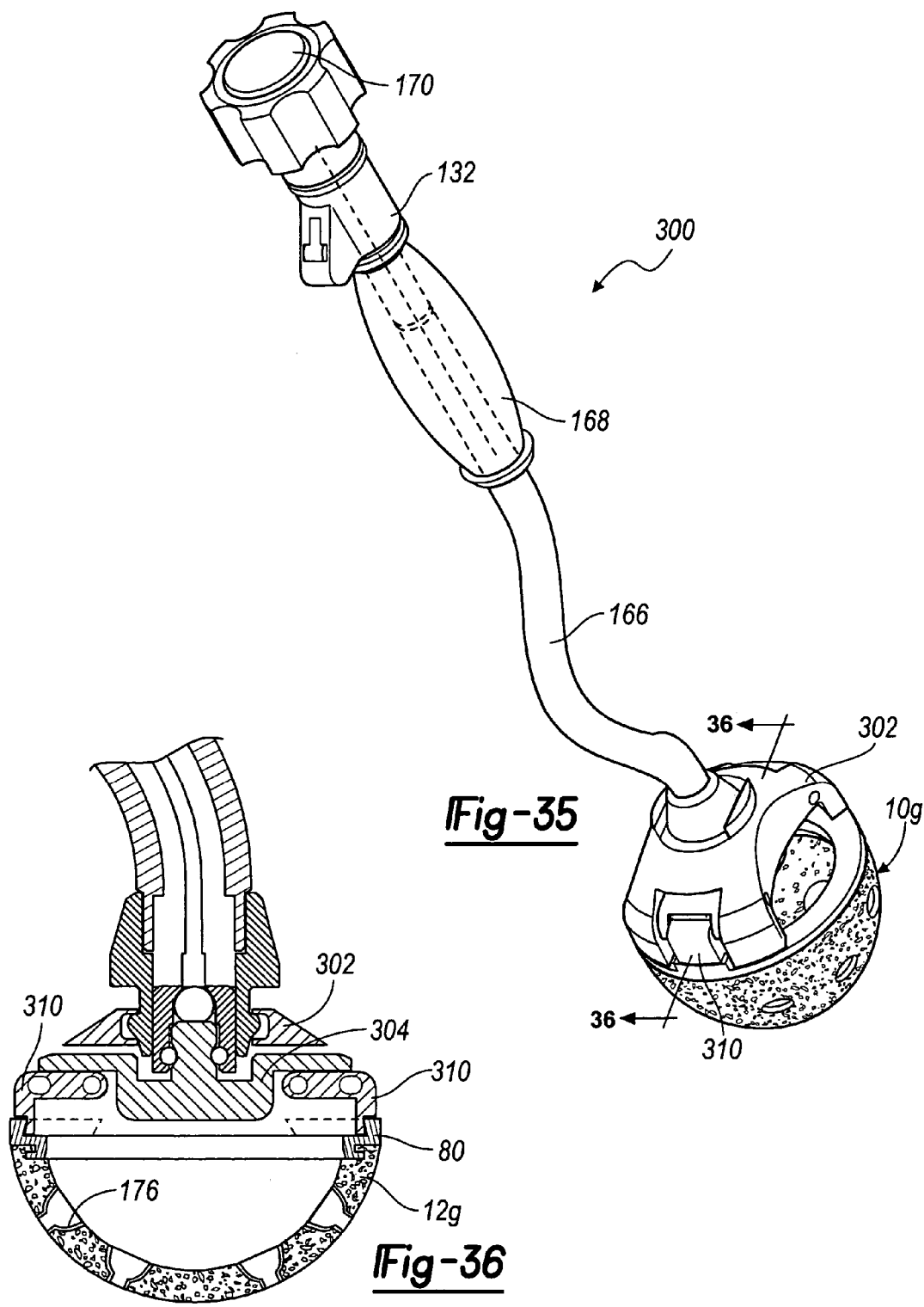

METHOD AND APPARATUS FOR USE OF POROUS IMPLANTS

This application is a continuation-in-part of U.S. patent application Ser. No. 11/294,692, filed Dec. 5, 2005, which is a continuation-in-part of U.S. patent application Ser. No. 11/111,123, filed Apr. 21, 2005. The disclosures of the above applications are incorporated herein by reference.

FIELD

The present invention relates to porous implants and more particularly to porous implants for promoting bone growth used in load bearing applications, anchoring or as augments for replacing removed portions of bone.

INTRODUCTION

Porous coated implants have been used to promote biologic fixation of surrounding bony tissue. In one example, porous material may be coated on an exterior surface of a prosthetic implant to encourage ingrowth of surrounding bone into the pore spaces of the porous material. Typically, the porous coating may comprise stainless steel, titanium, titanium alloys, tantalum, cobalt-chromium alloys, ceramics, polymers and other materials that are suited for use in a biocompatible environment. Various joining methods have been employed to attach the porous coating to a desired prosthetic implant. For example, soldering, brazing, adhesive joining, laser welding, diffusion bonding, metallurgic bonds and mechanical joining have been shown to suitably attach the porous material to a desired implant.

SUMMARY OF THE INVENTION

An orthopedic prosthesis for implantation into a bone of a patient includes a porous metal shell adapted to be affixed within the bone. The porous metal shell includes an outer surface adapted to receive bone ingrowth after the implantation and an inner surface adapted to engage a liner. The porous metal shell is porous from the outer surface to the inner surface. A non-porous member may be affixed to the porous metal shell.

According to various features, the non-porous feature includes at least one piercing member extending from the outer surface, the piercing member adapted to penetrate the bone in an implanted position. The non-porous features may include spikes or fins. In one example, the piercing member may define a reduced material cross section at an interface with the outer surface of the porous metal shell. The piercing member may be adapted to be broken at the reduced material cross section and removed from the porous metal shell.

An orthopedic prosthesis for implantation into a bone of a patient includes an integrally formed shell having an outer portion comprising a first porous layer adapted to receive bone ingrowth after implantation. An inner portion includes a second porous layer and an intermediate portion includes a solid membrane. A fixation member may be adapted to be interoperatively inserted through the shell from the inner portion to the outer portion and pierce the solid membrane. The solid membrane may be adapted to inhibit particles from migrating from the inner portion to the outer portion.

According to various features, a bearing liner may be affixed to the inner portion. The integrally formed shell may define a hemispherical section wherein the fixation member may be adapted to be received at any desired location around the hemispherical section. According to other features, the first and second porous layer may define preformed passages adapted to accept a fastener therethrough.

An orthopedic prosthesis for implantation into a bone of a patient includes an integrally formed shell having an outer portion, an inner portion and an intermediate portion. The outer portion comprises porous metal adapted to receive bone ingrowth after implantation. The inner portion comprises ceramic and defines a bearing surface. The intermediate portion comprises a transition layer. The transition layer may comprise at least one of powdered metal and ceramic. According to other features, the intermediate layer may encapsulate the inner portion.

An orthopedic prosthesis for implantation into a bone of a patient includes a porous metal shell adapted to be affixed within the bone. The porous metal shell defines continuous porous metal from an inner surface to an outer surface, the outer surface adapted to receive bone ingrowth after the implantation. A non-porous rim may be affixed to a radial edge of the porous metal shell at an interface surface.

According to additional features, the interface surface may define a metallurgical bond. The radial edge of the porous metal shell may define a first annular pocket receiving a portion of the non-porous rim. The non-porous rim may define a second annular pocket receiving a portion of the porous metal shell. The non-porous rim may define a raised wall adapted to mate with an attachment tool. The raised wall may define a tapered cross-section adapted to securably mate with a complementary tapered cross-section defined on the attachment tool. According to other features, an annular ring may be selectively located within an annular groove formed on the inner surface of the porous metal shell. The annular ring may be adapted to capture a bearing liner within the porous metal shell.

Further areas of applicability of the present invention will become apparent from the detailed description provided hereinafter. It should be understood that the detailed description and specific examples, while indicating the preferred embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1 is a perspective view of a porous metal cup incorporating solid features according to the present teachings;

FIG. 1A is a detail view of an exemplary solid plug defining an apical hole of the porous metal cup of FIG. 1;

FIG. 2 is an assembly sequence illustrating an exemplary method of affixing the solid features of FIG. 1 to the porous metal cup;

FIGS. 3-6 are perspective views of porous metal cups incorporating solid features according to additional features;

FIG. 18 is a perspective view of the assembly tool of FIG. 15 cooperating with an exemplary impaction handle;

FIG. 19 is a sectional view of FIG. 18 taken along line 19-19;

FIG. 35 is a perspective view of the assembly tool of FIG. 32 cooperating with an exemplary impaction handle;

FIG. 36 is a sectional view of FIG. 35 taken along line 36-36;

DETAILED DESCRIPTION OF THE PREFERRED EMBODIMENTS

The following description of the embodiment(s) is merely exemplary in nature and is in no way intended to limit the invention, its application, or uses. Furthermore, while the present teachings are described in association with an acetabular cup for a hip joint, those skilled in the art will appreciate that the present teachings may be incorporated into various orthopedic implants for a human body such as knee, shoulder, and other joints. Therefore, it is to be understood that the present illustrative embodiments are not meant to limit the present invention.

Figure 4:
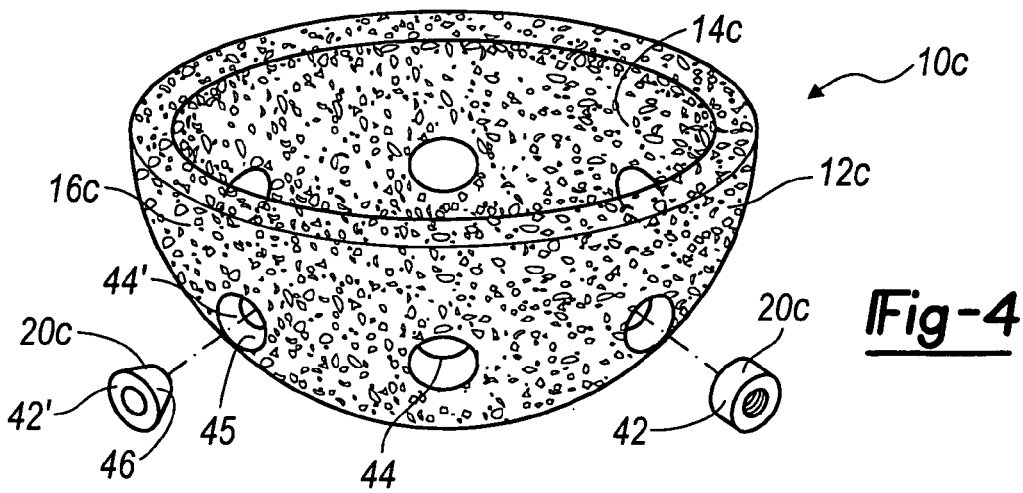
Figure 5:
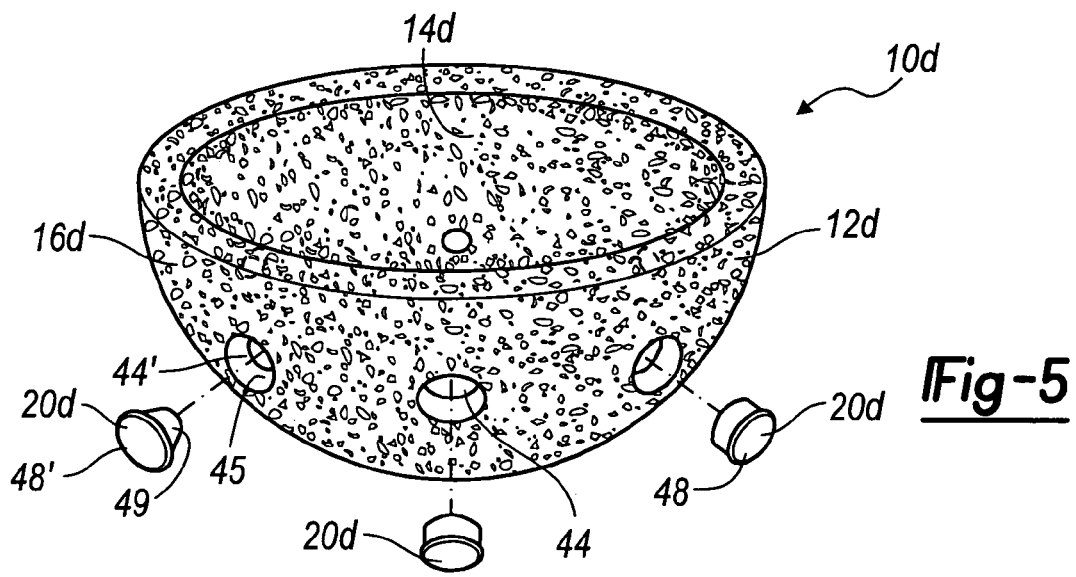
Figure 6:
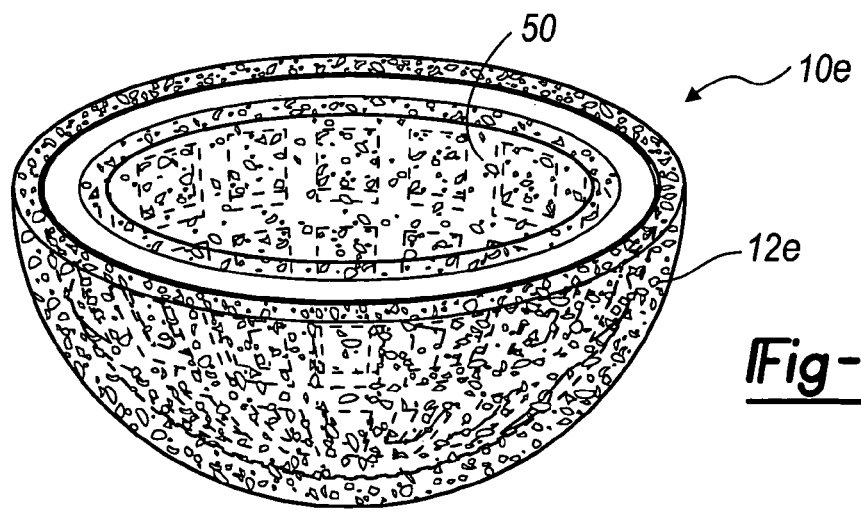

With reference to FIGS. 1-6, a series of acetabular cups constructed in accordance to the present teachings are shown and generally identified at reference numerals $10a$-$10e$. The acetabular cups $10a$-$10e$ generally define a shell $12a$-$12e$ having an inner surface $14a$-$14e$ and an outer surface $16a$-$16e$. A plurality of solid features $20a$-$20e$ are arranged around the outer surface $16a$-$16d$ of the shell $10a$-$10d$ (FIGS. 1-5), or within the shell $10e$ (FIG. 6). In one example, the shells $12a$-$12e$ may be formed entirely of porous metal 22 extending from the inner surface $14a$-$14d$ to the outer surface $16a$-$16d$. The porous metal 22 may comprise stainless steel, titanium, titanium alloys, cobalt-chromium alloys and other materials that are suited for use in a biocompatible environment. The solid features $20a$-$20e$ may be formed of non-porous material such as stainless steel, titanium, titanium alloys, cobalt-chromium alloys and other materials that are suited for use in a biocompatible environment. The outer surface $16a$-$16e$ may be adapted to receive bone ingrowth after implantation. According to some embodiments (FIGS. 1-3), the solid features $20a$-$20b$ extending from the outer surface $16a$-$16b$ are adapted to penetrate bone in an implanted position. As will be described in greater detail, the solid features $20a$-$20d$ may be molded into the porous metal cup $10a$-$10d$ or added in a subsequent joining step.

With specific reference to FIG. 1, the solid features $20a$ may comprise a plurality of piercing members or spikes 28. The spikes 28 may be molded into the porous metal cup $10a$ as shown in FIG. 1, or alternatively, affixed to the porous metal cup $10a$ in a subsequent joining step as shown in FIG. 2. In one example, apertures 30 may be formed such as by a drill bit 32. A proximal shank 34 of the spike 28 may then be inserted through the apertures 30 and secured such as by adhesive or welding. In one example, some or all of the spikes may have a reduced material thickness at an interface with an outer surface of the porous metal cup $10a$ (see shank 29 provided on spike 28'). As such, some or all of these spikes may be broken away from the porous metal cup $10a$ such as by hand or with an impacting tool. A solid plug 36 (FIG. 1A) defining an apical hole may be threaded for mating with a cup insertion instrument. While the solid plug 36 is specifically shown on the porous metal cup $10a$, the solid plug 36 may be provided on any acetabular cup disclosed herein.

With reference to FIG. 3, the porous metal cup $10b$ having inner surface $14b$ and outer surface $16b$ is shown. The plurality of solid features $20b$ may comprise fins 38 molded into the porous metal cup $10b$. The fins 38 may be arranged around the outer surface $16b$ of the shell $12b$. The fins 38 generally define a planar section 40 extending outwardly from the outer surface $16b$ of the shell $12b$. While not specifically shown, the fins 38 may alternatively be affixed to the porous metal cup $10b$ in a subsequent joining step as described with respect to porous metal cup 10a (FIG. 2). In one example, some of the fins 38 may be broken away from the outer surface 16b of the shell 12b interoperatively. Similar to the break away spikes 28' described above, some or all of the fins may have a reduced material thickness at an interface with an outer surface of the porous metal cup 10a (see finger 39 provided on fin 38'). As such, some or all of these fins may be broken away from the porous metal cup 10a such as by hand or with an impacting tool.

As illustrated in FIG. 4, the solid features 20c may include cannulated cylinders 42 adapted to be received in bores 44 defined through the shell 12c. Again, the solid features 20c may be molded with the porous metal shell 12c or alternatively, added subsequent to formation of the porous metal shell 12c. In this way, the plurality of bores 44 may be defined during a molding step of the porous metal shell 12c or formed through a machining operation such as drilling (see e.g. FIG. 2). The cannulated cylinders 42 may be affixed to the shell 12c by any suitable method such as adhesive or welding. In one example, the cannulated cylinders may be adapted to receive fasteners such as bone screws through bores 44 during implantation. In one example, an inner diameter 45 of a bore 44' and an outer diameter 46 of a cannulated cylinder 42' can be tapered to facilitate a compression fit.

FIG. 5 illustrates the porous metal cup 12d having inner surface 14d and outer surface 16d. The plurality of solid features 20d may comprise grommets 48. In one example, the grommets 48 may be used interoperatively to form a barrier at unused bores 44 in the shell 12d. In one example, an inner diameter 45 of a bore 44' and an outer diameter 49 of a grommet 48' can be tapered to facilitate a compression fit.

FIG. 6 illustrates a hemispherical webbing 50 integrally formed during a molding step with the porous metal shell 12e. The hemispherical webbing 50 may comprise a non-porous biocompatible metal such as titanium. The hemispherical webbing 50 may be adapted to provide structural support to the porous metal shell 12e.

Figure 8:
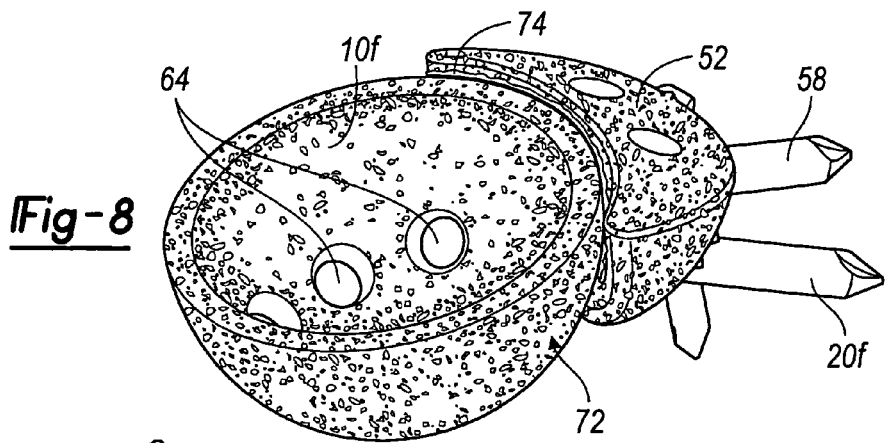
FIGS. 8 and 9 are perspective views of the exemplary porous metal augment of FIG. 7 shown cooperating with an exemplary porous metal shell.
Figure 9:
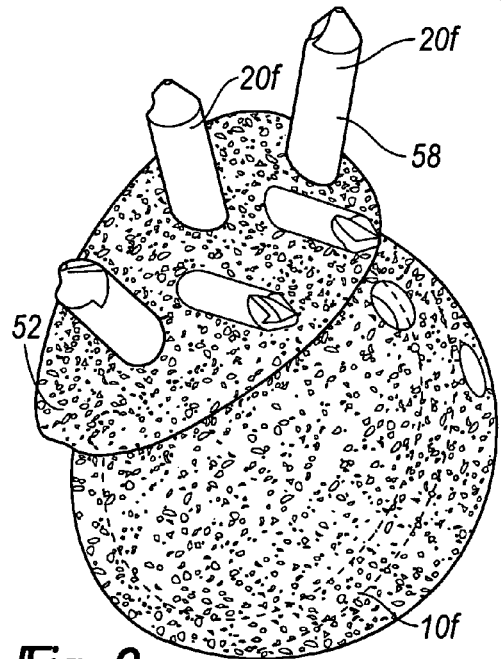
Figure 7:
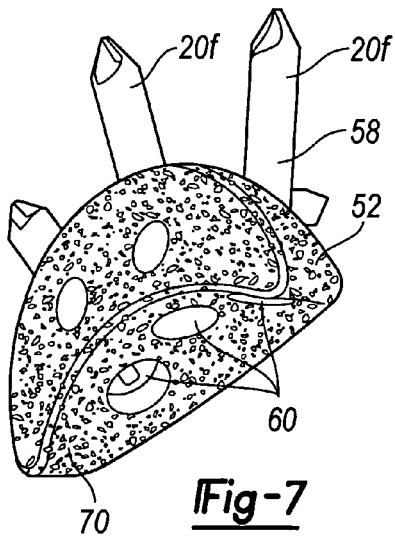
FIG. 7 is a perspective view of an exemplary porous metal augment according to the present teachings.
Figure 7A:
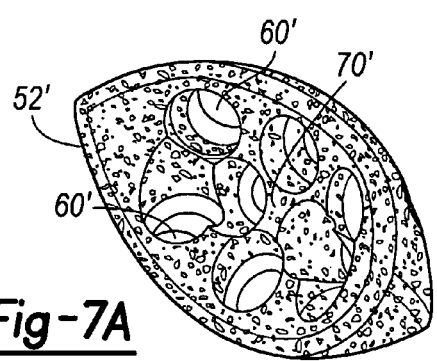
Figure 7B:
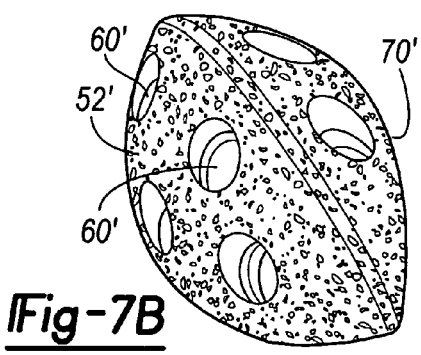

With reference to FIG. 7, an augment 52 is shown. The augment 52 may be formed of porous metal such as by one of the materials disclosed herein. A series of solid features 20 such as bone spikes or screws 58 are shown extending from the augment 52. In one example, the bone screws 58 may be inserted interoperatively through a series of bores 60 (FIG. 7) provided through the augment 52. A series of augments having various sizes and/or porosity may be provided. FIGS. 8 and 9 illustrate the augment 52 adjacent an acetabular cup 10f. The acetabular cup 10f may be formed of porous metal such as described herein. A series of apertures 64 may be formed on the acetabular cup 10f for receiving fasteners (not specifically shown) during implantation. The configuration and orientation of the apertures 64 are merely exemplary. It is appreciated that the augments shown may alternatively be used with other acetabular cups such as those disclosed herein. As shown, an outer radial wall 70 (FIG. 7) of the augment 52 cooperates with an outer radial wall 72 of the cup 10f in a side by side relationship. In one example poly methyl methacrylate (PMMA) bone cement 74 may be used to join the augment 52 to the acetabular cup 10f. Other joining techniques may also be used such as mechanical fastening. The augment 52 may be used to fill an area adjacent the acetabular cup 10f such as where a bone defect was removed.

An exemplary method of making the acetabular cups 10a-10f according to the present teachings will now be described. In one example, a mixture of metallic powder, such as titanium powder or cobalt-chromium alloy powder, and a binder, such as ammonium bicarbonate or d-limonene may be combined together into a homogeneous mixture. In one example, the metallic powder and binder may be placed into a containment device such as a bag and sealed. The bags may then be placed into a cold isostatic press (CIP) defining an inverse acetabular shell and pressure applied. The CIP shapes the mixture into an acetabular shell. The solid features 12a-12e may be molded-into the porous metal concurrently with the CIP, or alternatively be added after such as by a machining operation. The acetabular cup 10a-10f may then be placed into a furnace and baked for a predetermined timeframe suitable to burn off the binder. One exemplary cycle includes 400 degrees C. for 12 hours. If necessary, a subsequent machining step may be performed on the solid features 12a-12e. Other exemplary methods for making porous acetabular cups may be found in application, U.S. patent application Ser. No. 11/357,929, filed Feb. 17, 2006 filed concurrently herewith, entitled "Method and Apparatus for Forming Porous Metal Implants", also assigned to Biomet Manufacturing Corp., of Warsaw Ind., which is incorporated herein by reference. In one exemplary method, described in U.S. Ser. No. 11/357,929, utilizing a ratio of metal powder to spacing agent of 8:1 will provide an dense acetabular cup having very fine pores. In another example, in a mixture having a 3:1 metal powder to spacing agent ratio, if the spacing agent has a diameter of at least about 25 micrometers and the metal powder has a diameter of about 10 micrometers, large pores result. If the metal powder and spacing agent diameter sizes were reversed, smaller pores would result.

Figure 10:
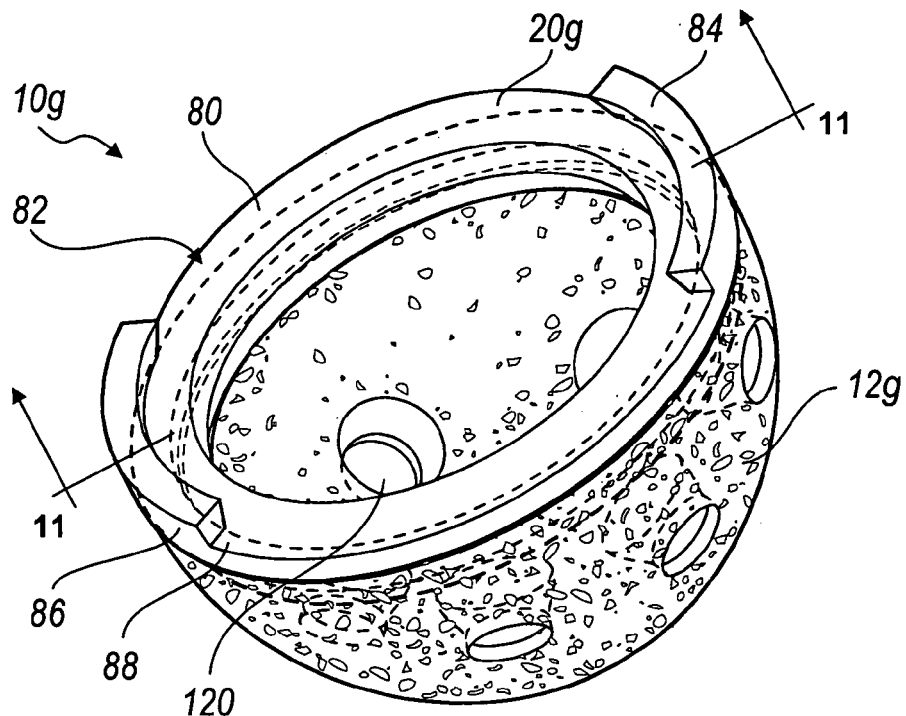
FIG. 10 is a perspective view of a porous metal shell incorporating a solid metal rim according to additional features.
Figure 11:
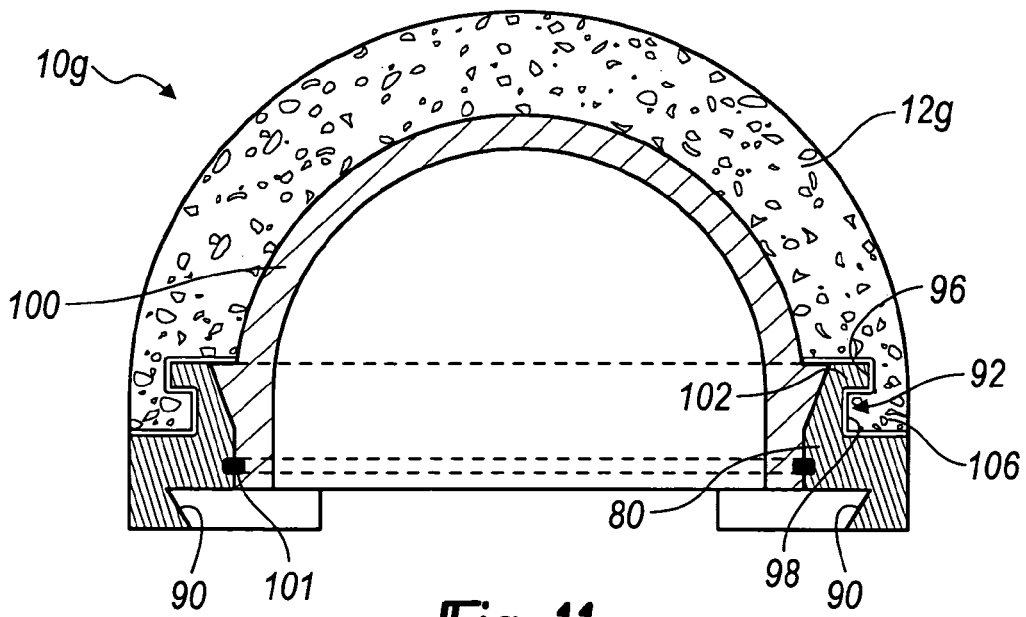
FIG. 11 is a sectional view of the porous metal shell of FIG. 10 taken along line 11-11.

Turning now to FIGS. 10 and 11 an acetabular cup 10g having a porous metal shell 12g and an integrally molded solid feature 20g in the form of a solid ring or rim 80 is shown. The solid ring 80 may be formed of biocompatible metal such as, but not limited to, solid titanium or titanium alloy. An outer face 82 of the solid ring 80 defines an attachment feature 84 in the form of raised walls 86 extending from a planar surface 88. The raised walls 86 each define a first tapered surface 90 (FIG. 11). As will be described, the raised walls 86 mate with complementary structure provided on an attachment tool during implantation.

With specific reference to FIG. 11, an interface surface 92 between the porous metal shell 12g and the solid ring 80 is shown. A metallurgical bond is created at the interface surface 92 during formation of the acetabular cup 10g as will be described in greater detail. A first annular pocket 96 is defined around an inner radius of the porous metal shell 12g. Similarly, a second annular pocket 98 is defined around an outer radius of the solid ring 80. A first collar 102 formed on the solid ring 80 nests in the first annular pocket 96 of the porous metal shell 12g. A second collar 106 formed on the porous metal shell 12g nests in the second annular pocket 98 of the solid ring 80. The respective pockets 96 and 98 and collars 102 and 106 provide an overhanging interlock between the porous metal shell 12g and the solid ring 80 for increased structural integrity. As illustrated in FIG. 11, a liner 100 is shown captured within the porous metal shell 12g by an annular ring 101.

Figure 12:
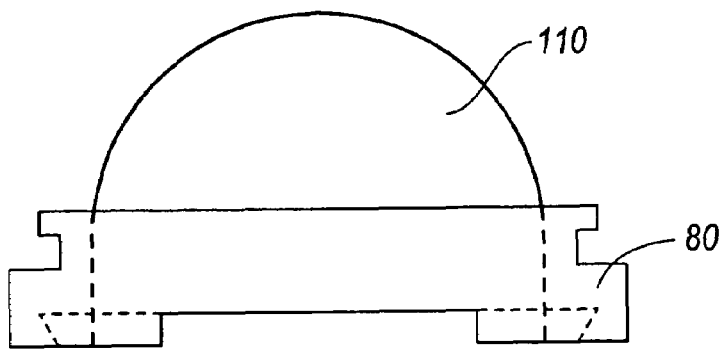
FIG. 12 is a side view of an exemplary assembly step wherein the solid metal rim is placed around a dome.
Figure 13:
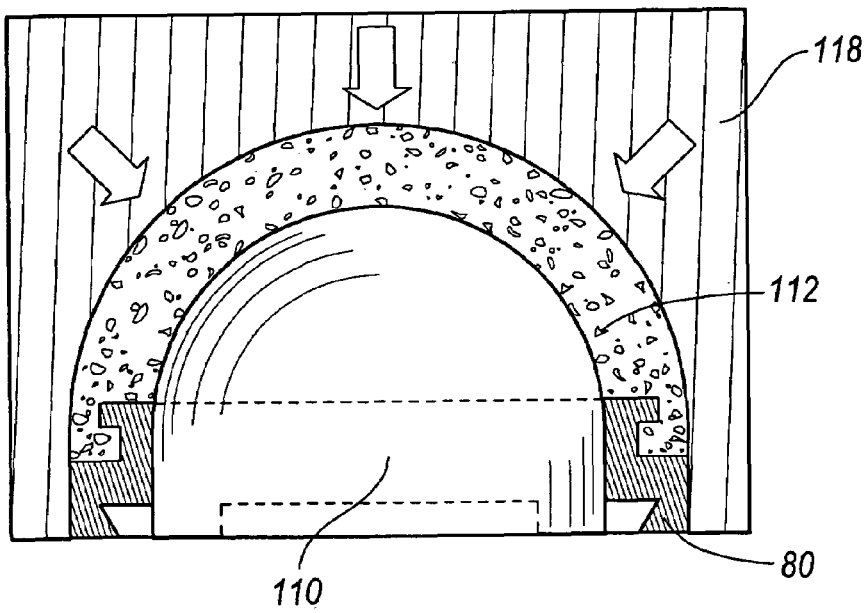
FIG. 13 is an exemplary assembly step wherein a porous metal concentration is arranged in a cold isostatic press with the solid metal rim.
Figure 14:
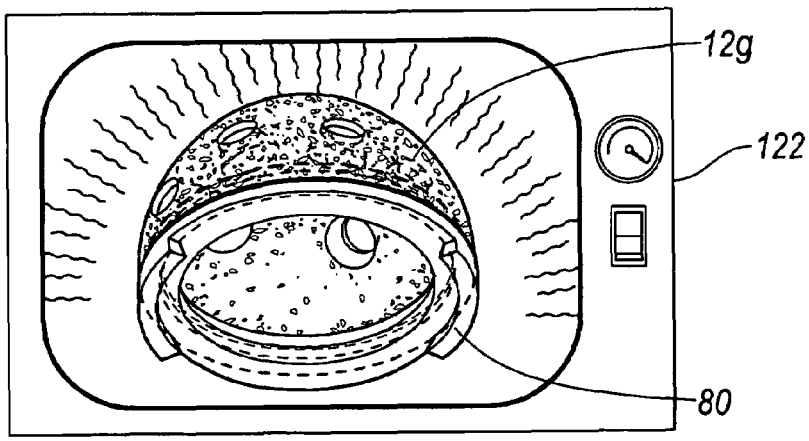
FIG. 14 illustrates an exemplary assembly step wherein the porous metal shell and solid rim are placed within a furnace.

With reference to FIGS. 12-14, an exemplary method of making the acetabular cup 10g according to the present teachings will now be described. In one example, a blank of solid metal may be initially machined into the solid metal ring 80. Next, the machined ring 80 may be located over a dome 110 (FIG. 12). A mixture of metallic powder and binder 112 is then prepared into a homogeneous mixture as described above. The mixture of metallic powder and binder 112 may be placed into a containment member such as a bag (not specifically shown) and located over the dome 110 and solid metal ring 80 in a CIP 118. The CIP 118 applies high pressure onto the mixture 112 and solid metal ring 80 to form a metallurgical bond at the interface surface 92. The porous metal shell 12g and solid metal ring 80 assembly are then removed from the CIP 118. The porous metal shell 12g may present a hard, wet sandy consistency. The porous metal 12g shell may then be machined to create a uniform thickness around its semi-hemisphere. Passages 120 (FIG. 10) may also be machined. It is contemplated that the passages 120 may be alternatively formed by extensions located on the dome 110 during the CIP process. It is appreciated that a combination of some or all of the other solid features may be molded to the porous metal shell.

The assembly (porous metal shell 12g and solid ring 80) may then be placed into a furnace 122 and baked for a pre-determined timeframe suitable to burn off the binder. An exemplary cycle includes 400 degrees C. for 12 hours. The solid 80 ring may be subsequently machined if necessary to define the desired shape. The augment 52 may be formed utilizing similar steps as described above.

Figure 15:
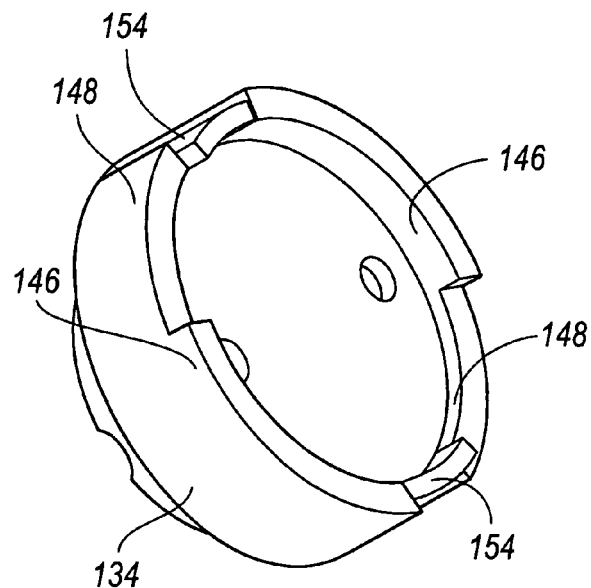
FIG. 15 illustrates an assembly tool according to the present teachings adapted to mate with the solid metal rim during implantation.
Figure 16:
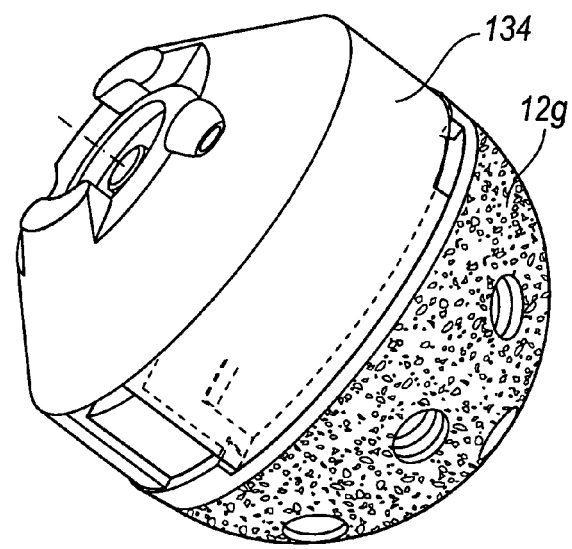
FIG. 16 illustrates the assembly tool of FIG. 15 shown mated with the solid metal rim.
Figure 17:
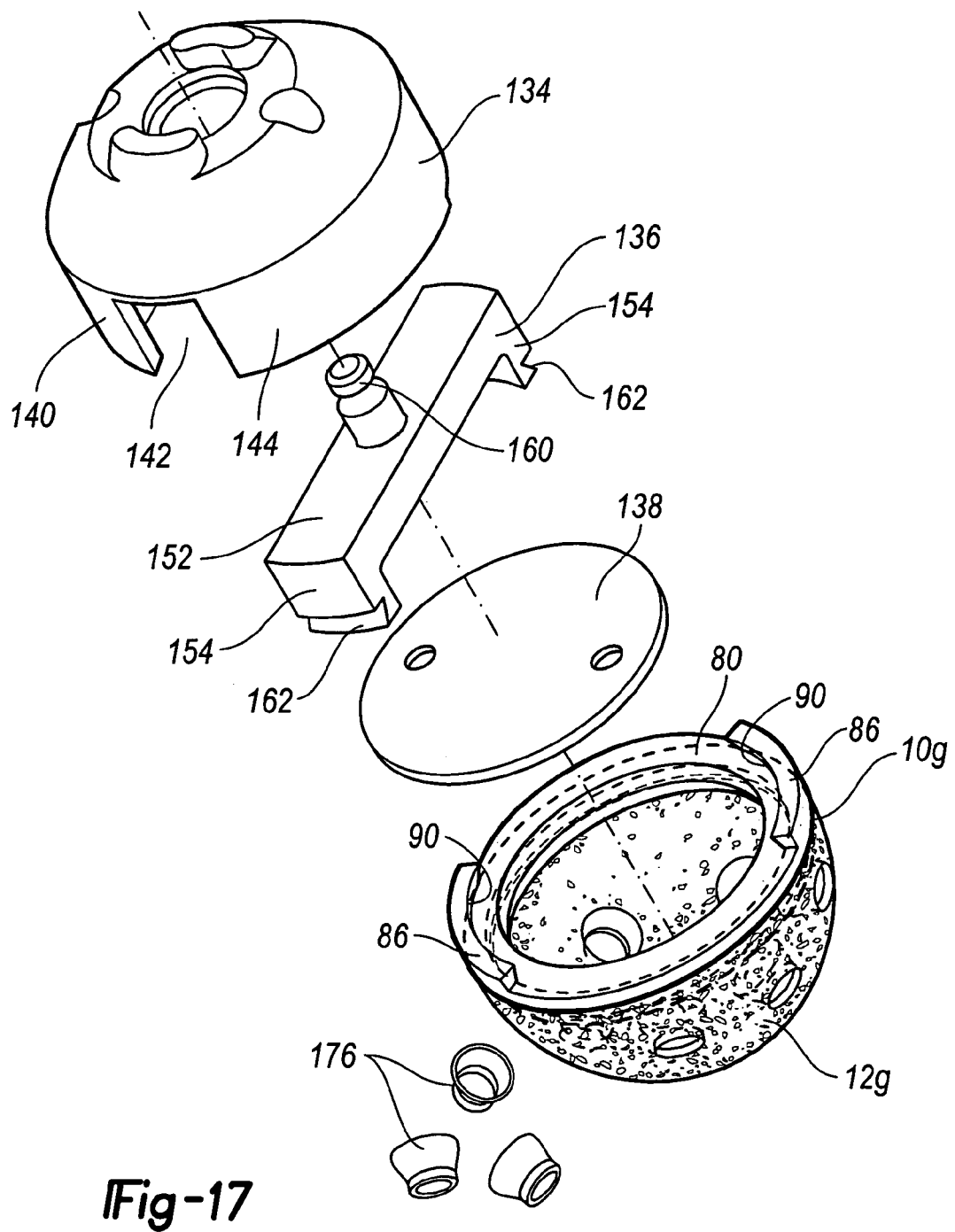
FIG. 17 is an exploded view of the assembly tool of FIG. 15 shown with the porous metal cup.

With reference now to FIGS. 15-19, an exemplary implantation tool 130 (FIG. 18) will be described. The implantation tool 130 generally includes a handle 132, a housing 134, a T-bar 136 (FIG. 17) and a plate 138. The housing 134 can include a cup portion 140 having a pair of passages 142 defined through a radial wall (FIG. 17). The housing 134 can define a pair of raised wall portions 146 and a pair of recessed wall portions 148 (FIG. 15). The T-bar 136 can include a longitudinal portion 152 (FIG. 17) having fingers 154 extending on opposite ends. A shaft portion 160 extends centrally from the longitudinal portion 152 in a direction opposite the fingers 154. The shaft portion 160 is adapted to cooperate with a driver as will be described in greater detail later. The fingers 154 nest in the passages 142 of the housing 134. The T-bar 136 is operable to move axially relative to the housing 134 along the passages 142 to facilitate a gripping action onto the solid ring 80. More specifically, the fingers 154 of the T-bar 136 each define second tapered surfaces 162 (FIG. 17) adapted to mate With the first tapered surfaces 90 of the raised walls 86 on the solid ring 80 (FIG. 19). Once the respective tapered surfaces 90, 162 engage, the T-bar 136 may be translated axially away from the acetabular cup 10g thereby creating tension between the respective tapered surfaces 90, 162. The plate 138 may be adapted to locate within an annular space defined by the cup portion 140.

With specific reference to FIGS. 18 and 19, the handle 132 will now be described in greater detail. The handle 132 generally includes a gripping member 168 disposed along a longitudinal shaft portion 166 and a knob 170 having an impacting surface. Rotation of the knob 170 communicates axial movement to the T-bar 136 through a locking interface 172. While not specifically, shown, a core may be housed within the tool (near the knob 170) and threadably connected to the knob 170. A cable may connect the core with the locking interface 172. In this way, rotation of the knob results in axial movement of the T-bar 136. The locking interface 172 may comprise a quick connect or other suitable connection.

An exemplary method of using the implantation tool 130 will now be described. At the outset, the raised walls 146 of the cup portion 140 are aligned with the planar surface 88 of the solid ring 80. Next, the cup portion 140 and the T-bar 136 are rotated by way of the handle 132, such that the second tapered surfaces 162 of the fingers 154 slidably locate under the first tapered surfaces 90 of the raised walls 86 on the solid ring 80. In one example, the cup portion 140 and the T-bar 136 are rotated about 20 degrees clockwise to achieve an interlocking relationship. Next, the gripping member 168 is translated upward as viewed in FIG. 18 to create tension between the first and second tapered surfaces 90, 162 as described above. Once the installation tool 130 has securely retained the acetabular cup 10g, the acetabular cup 10g may be located into a desired location on the patient (not shown). The impacting surface of the knob 170 may then be struck with an impacting tool until the acetabular cup 10g has been implanted. Once the acetabular cup 10g has been implanted to a desired position, the handle 132 may be rotated in an opposite direction until the tapered surfaces 162 of the fingers 154 are disengaged with the tapered surfaces 90 of the raised walls 86 on the solid ring 80. The implantation tool 130 may then be removed.

It is appreciated that the acetabular cup 10g may be secured to the implantation site by any suitable methods such as fasteners through passages 120 and/or bone cement. Inserts 176 (FIG. 17) may optionally be placed through the passages 120 or molded therein.

Figure 20:
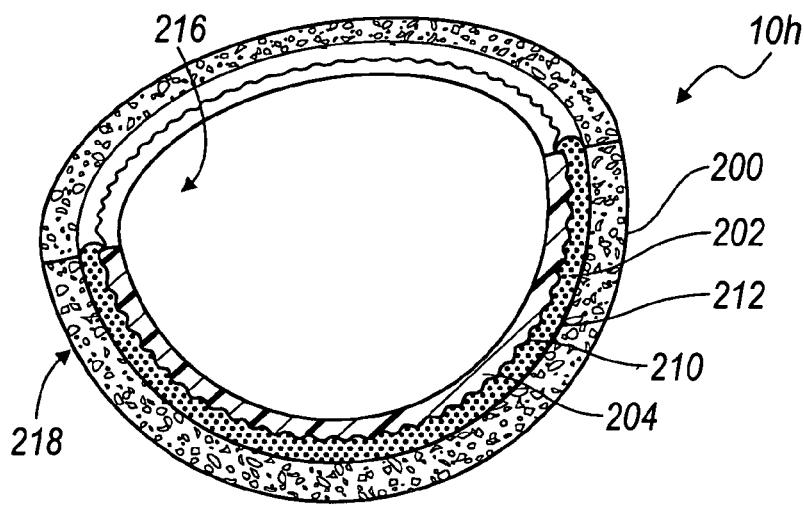
FIG. 20 is a cutaway view of a porous metal cup according to additional features.

Turning now to FIG. 20, an acetabular cup 10h according to additional features will be described. The acetabular cup 10h generally includes a porous metal outer layer 200, a pressed metal powder intermediate layer 202, and a solid ceramic inner layer 204. An exemplary method of making the acetabular shell 10h includes forming a solid ceramic insert 204 having a rough, or textured outer surface 210. Powdered metal may then be pressed onto the textured outer surface 210 of the ceramic insert 204. The pressed powdered metal 202 may define a thin cross-section relative to the inner ceramic layer 204 and the outer porous metal layer 200. The powdered metal 202 may comprise biocompatible metals such as those disclosed herein. A porous metal layer 200 may then be formed on an outer surface 212 of the pressed powdered metal 202. The porous metal layer 200 may comprise biocompatible metal such as those described herein. The porous metal layer 200 may be formed onto the pressed powdered metal layer 202 by any suitable method such as by CIP, as disclosed herein. The assembly may then be placed into a furnace and sintered. The resulting acetabular cup 10h is one-piece having a ceramic bearing surface 216 and a porous metal outer surface 218. The porous metal outer surface 218 facilitates bone ingrowth.

Figure 21:
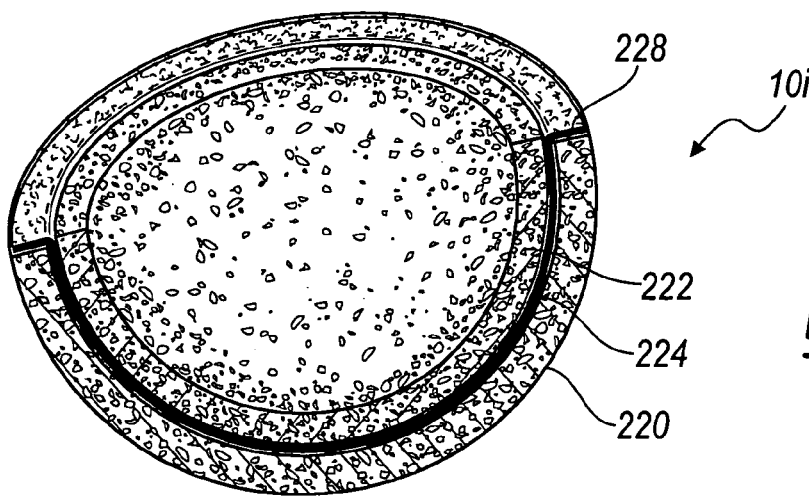
FIG. 21 is a cutaway view of a porous metal cup having a solid metal intermediate layer according to additional features.
Figure 22:
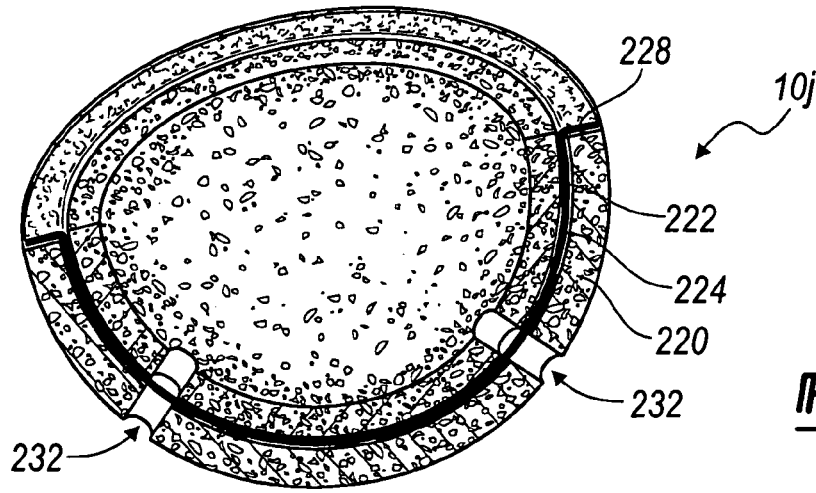
FIG. 22 is a cutaway view of the porous metal cup of FIG. 21 shown with predefined passages according to additional features.
Figure 23:
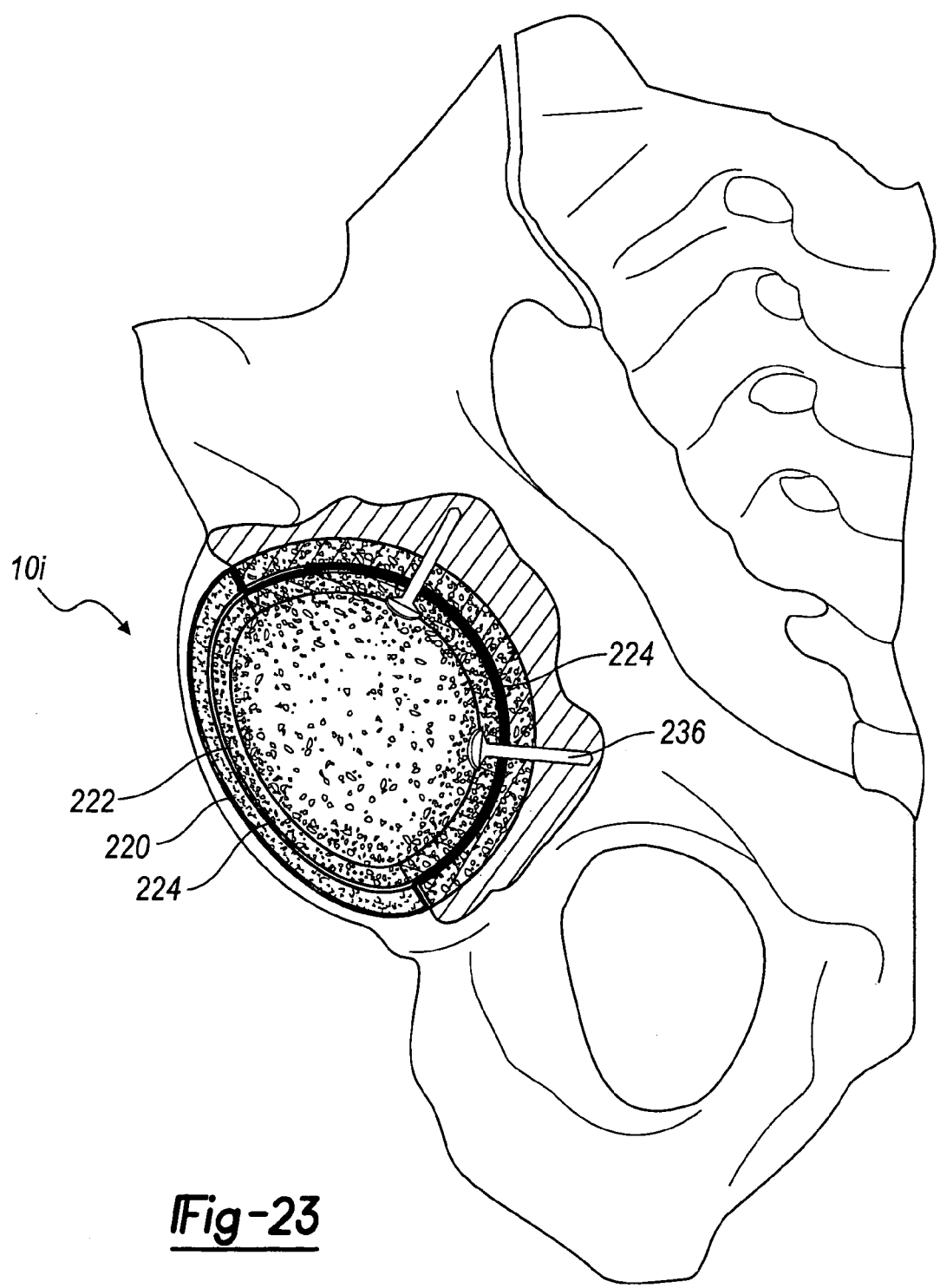
FIG. 23 is a partial perspective view of the porous metal cup of FIG. 21 shown in an implanted position.

With reference now to FIGS. 21-23, acetabular cups 10i and 10j constructed in accordance to additional features will be described. The acetabular cup 10i generally includes an outer porous metal layer 220, an inner porous metal layer 222 and a thin solid metal intermediate layer 224. In one example, the intermediate layer 224 may define an annular rim 228 around the outer porous metal layer 220. Again, the outer porous metal layer 220 is adapted to facilitate bone ingrowth. The inner porous layer 222 may be adapted to accept adhesive such as bone cement for cementing a liner. The inner porous layer 222 may be additionally or alternatively integrally molded with a polyethylene material.

The thin solid metal intermediate layer 224 is adapted to act as a barrier to inhibit migration of wear debris particles through the cup 10i and onto a bone-implant interface. In addition, the thin solid metal intermediate layer 224 may be pierced by a tool, such as a drill bit or fastener, such as a bone screw, intra-operatively for fixation at the implantation site. Because the intermediate layer 224 is uniform around the semi-hemisphere of the acetabular cup 10i, a surgeon is not limited to predefined, fixed locations for passing a fastener during implantation. Explained more clearly, the uniform intermediate layer 224 allows a surgeon to pass a fastener at any location around the semi-hemisphere of the acetabular cup 10i. In one example, screw holes (not shown) may be drilled intra-operatively through the acetabular cup 10i (FIG. 21). A surgeon may drill screw holes at locations that provide optimal fixation in the host bone without concern that wear particles will migrate onto the bone interface. In one example, the intermediate layer 224 defines a thickness less than 50%, or less than 25% of a thickness of the outer porous metal layer 220 and the inner porous metal layer 222, respectively.

In another example, screw holes 232 shown on acetabular cup 10*j* may be pre-defined through the inner and outer porous metal layers 220, 222 (FIG. 22), but closed at the solid intermediate layer 224. In this example, a surgeon may utilize some, or all of the pre-defined holes to pass bone screws through the solid intermediate layer. FIG. 23, illustrates the acetabular cup 10*i* in an implanted position secured with fasteners 236 pierced through the intermediate layer 224. While the solid intermediate layer 224 is specifically illustrated in the drawings as between the inner porous layer 222 and outer porous layer 220, the solid intermediate layer 224 may alternatively be formed on an inner concave surface of the cup 10*i*. In this way, the solid layer may provide a smooth surface for the bearing to ride.

Figure 24:
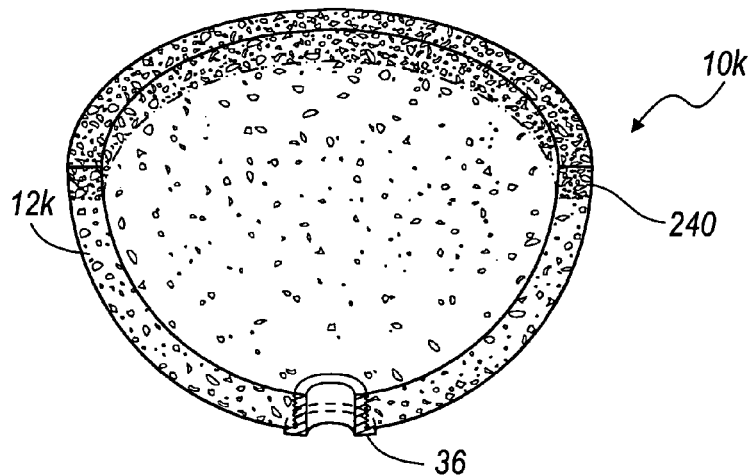
FIG. 24 is a sectional view of an exemplary porous metal cup according to additional features.
Figure 25:
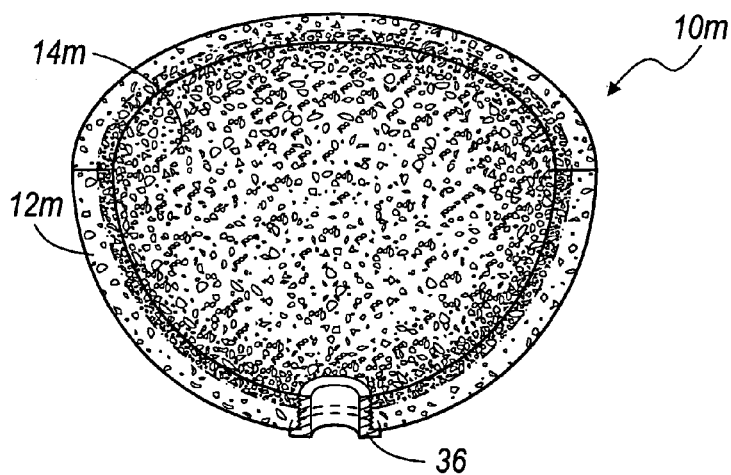
FIG. 25 is a sectional view of an exemplary porous metal cup according to additional features.

Turning now to FIGS. 24 and 25, acetabular cups 10*k* and 10*m* according to additional features are shown. Acetabular cups 10*k* and 10*m* are each formed of a porous metal shell 12*k* and 12*m* such as described herein. As illustrated, the porosity is less porous (or more dense) at a rim 240 of the acetabular cup 10*k*. In this way, the rim 240 may provide additional strength during implantation. In another example, the acetabular cup 10*k* is less porous (or more dense) at an inner surface 14*m* of the cup 10*m*. As a result, the acetabular cup 10*m* may provide additional strength at an interface with a bearing (not shown).

Figure 26:
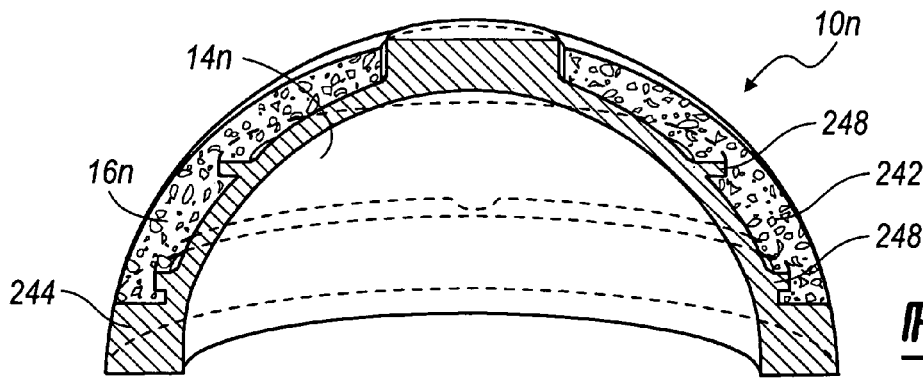
FIG. 26 is a perspective view of an exemplary porous metal cup according to additional features.
Figure 27:
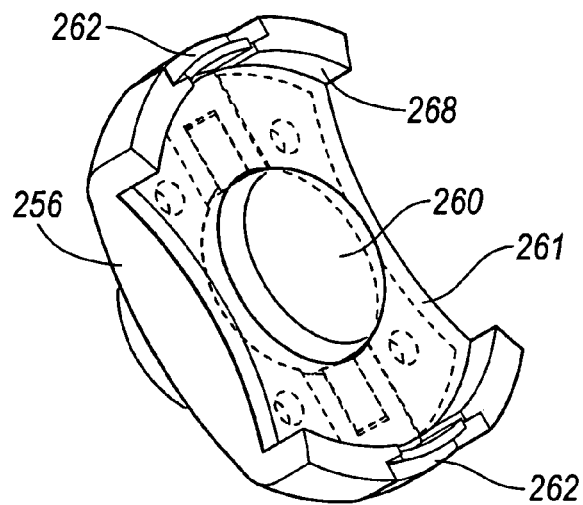
FIG. 27 illustrates an assembly tool according to the present teachings adapted to mate with the solid metal rim during implantation.
Figure 28:
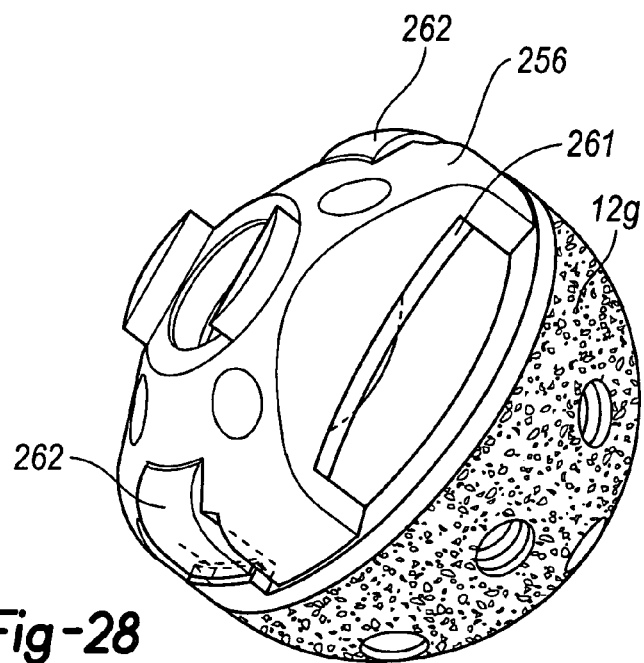
FIG. 28 illustrates the assembly tool of FIG. 27 shown mated with the solid metal rim.
Figure 29:
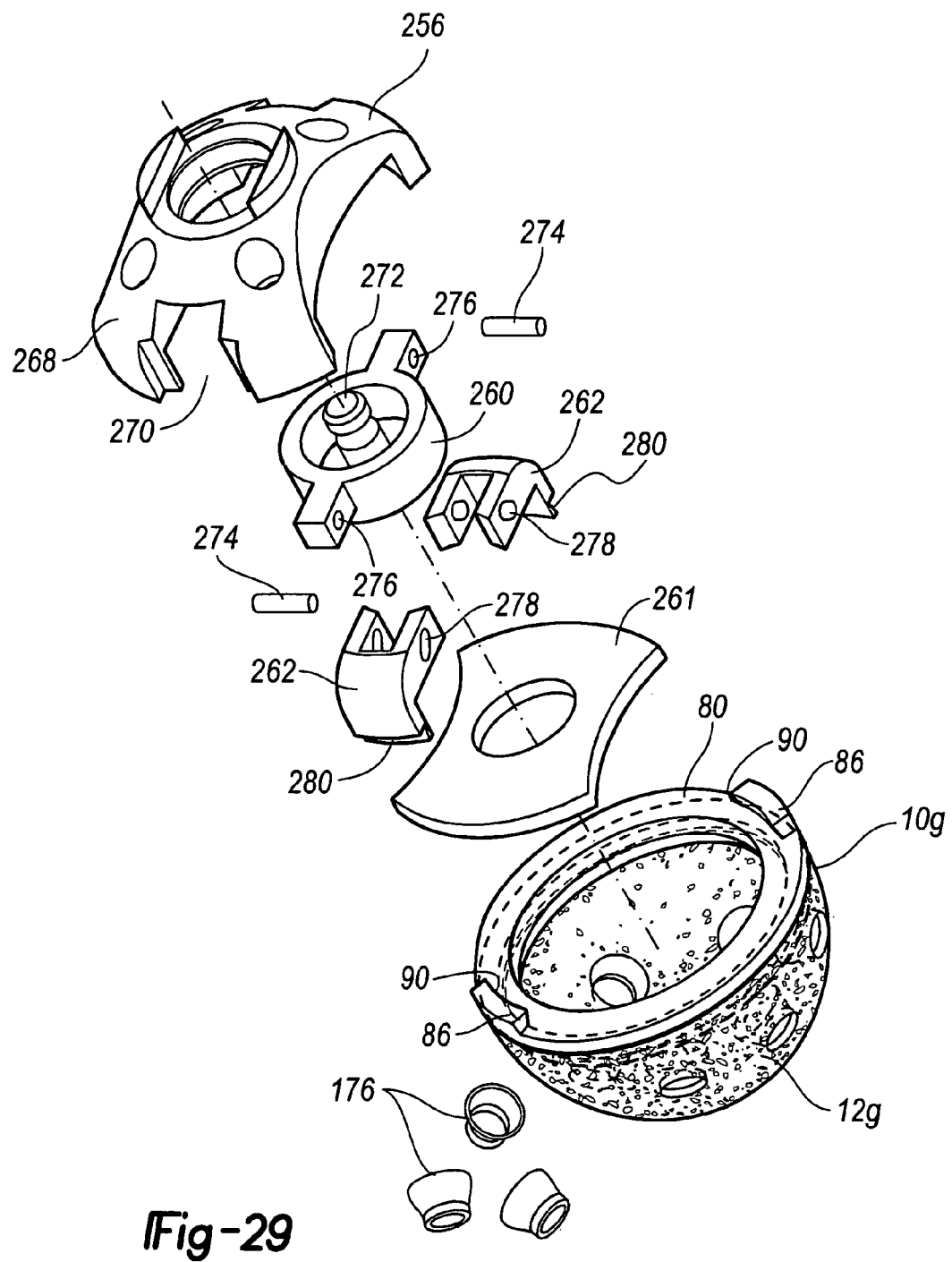
FIG. 29 is an exploded view of the assembly tool of FIG. 27 shown with the porous metal cup.

As illustrated in FIG. 26, another exemplary acetabular cup 0*n* is shown. The acetabular cup 10*n* generally includes a porous metal portion 242 and a solid metal portion 244. The porous metal portion 242 generally is formed on an outer surface 16*n* of the acetabular cup 10*n* while the solid metal portion 244 is formed on an inner surface 14*n*. The solid metal portion 244 defines a pair of annular lips 248 adapted to provide a secure mechanical interface with the porous metal portion 242. Alternatively, a single or a plurality of annular lips 248 may be formed on the solid metal portion 244. The porous metal and solid metal portions 242 and 244, respectively, may comprise biocompatible metal such as those disclosed herein. While not specifically shown, the solid metal portion 244 may include raised walls having tapered surfaces for mating with an installation tool such as disclosed herein.

Figures 30, 31:
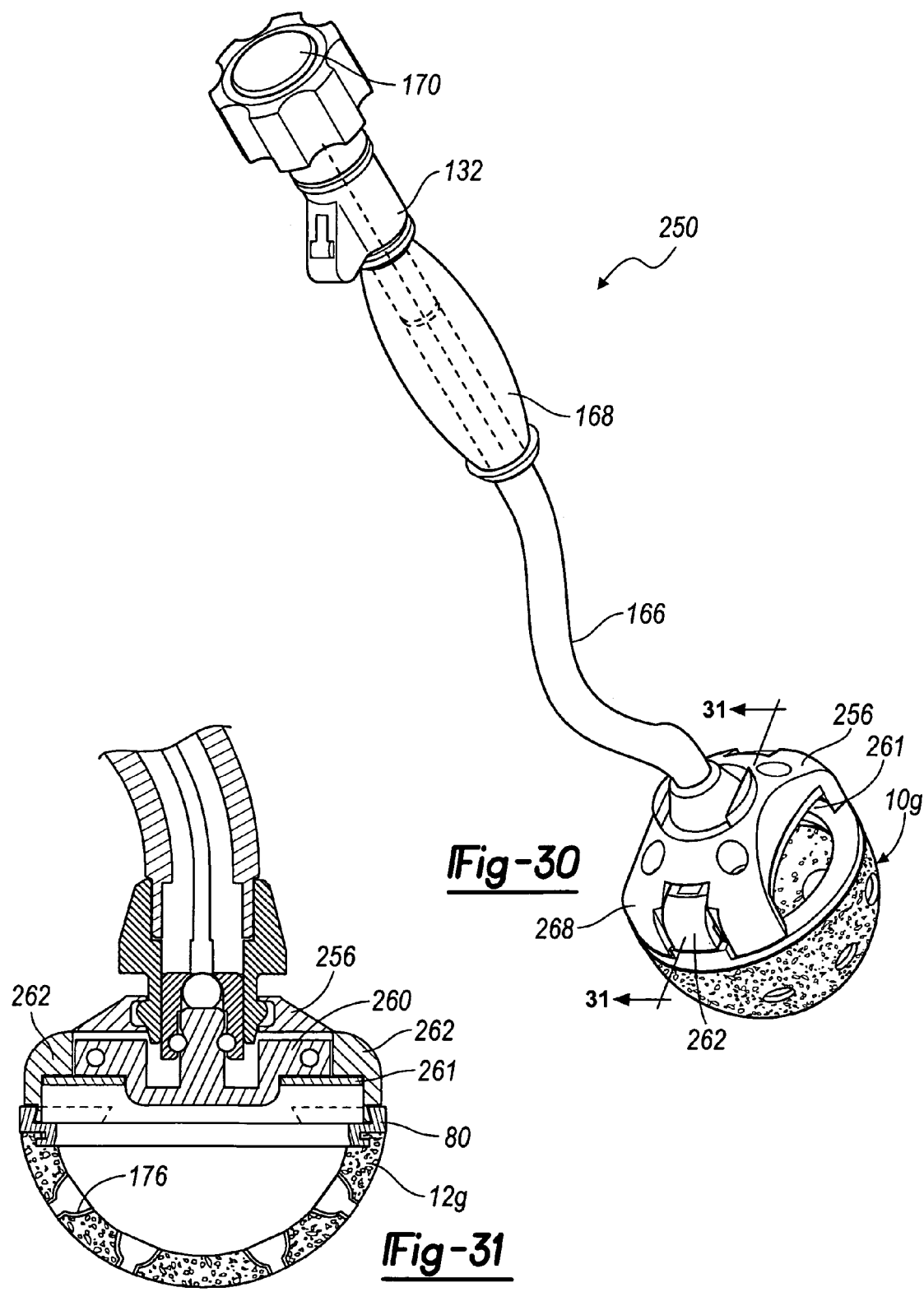
FIG. 30 is a perspective view of the assembly tool of FIG. 27 cooperating with an exemplary impaction handle.
FIG. 31 is a sectional view of FIG. 30 taken along line 31-31.
Figure 32:
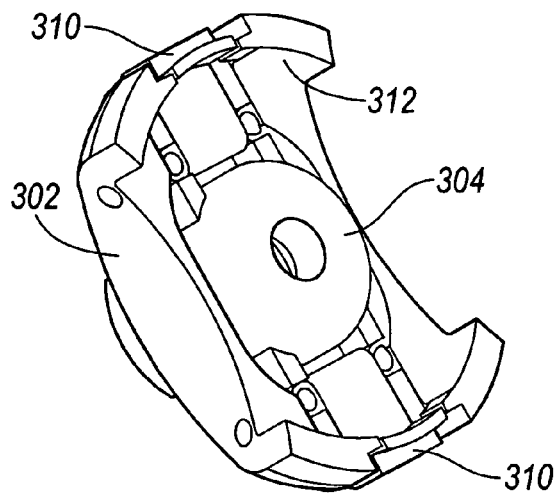
FIG. 32 illustrates an assembly tool according to the present teachings adapted to mate with the solid metal rim during implantation.
Figure 33:
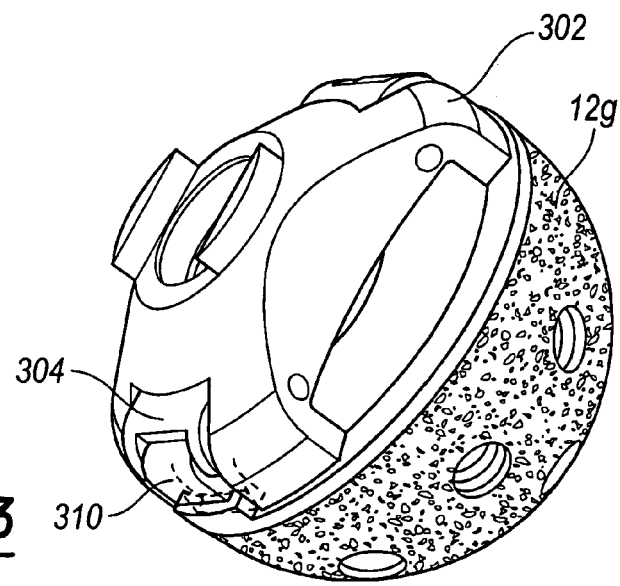
FIG. 33 illustrates the assembly tool of FIG. 32 shown mated with the solid metal rim.
Figure 34:
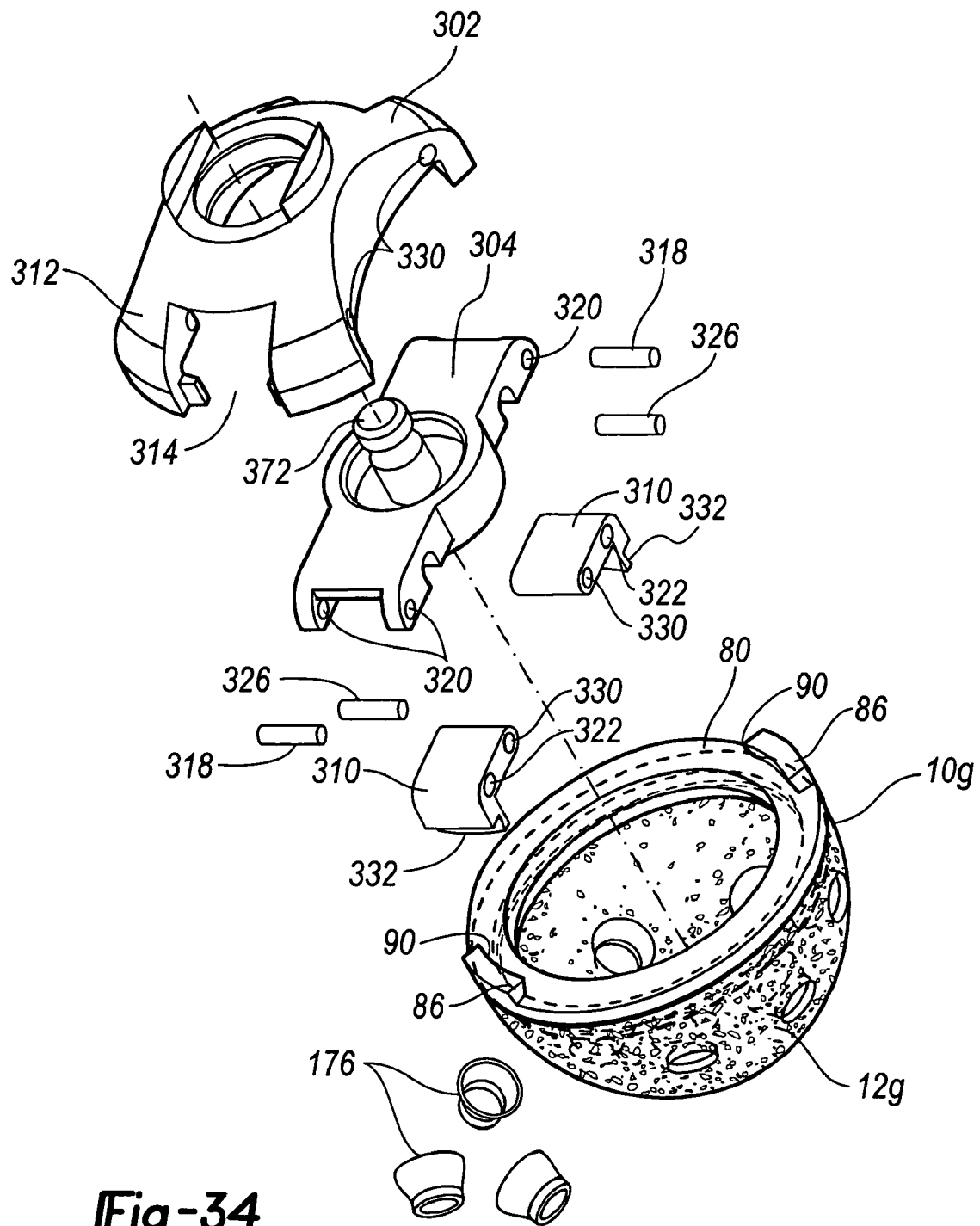
FIG. 34 is an exploded view of the assembly tool of FIG. 32 shown with the porous metal cup.
Figure 37:
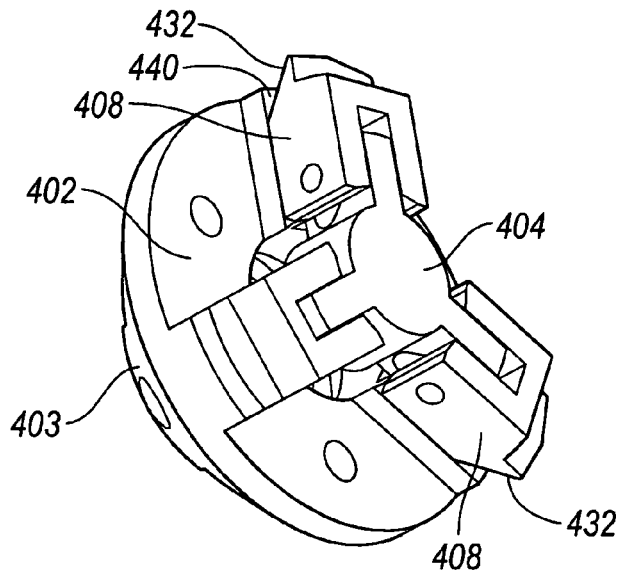
FIG. 37 illustrates an assembly tool according to the present teachings adapted to mate with the solid metal rim during implantation.
Figure 38:
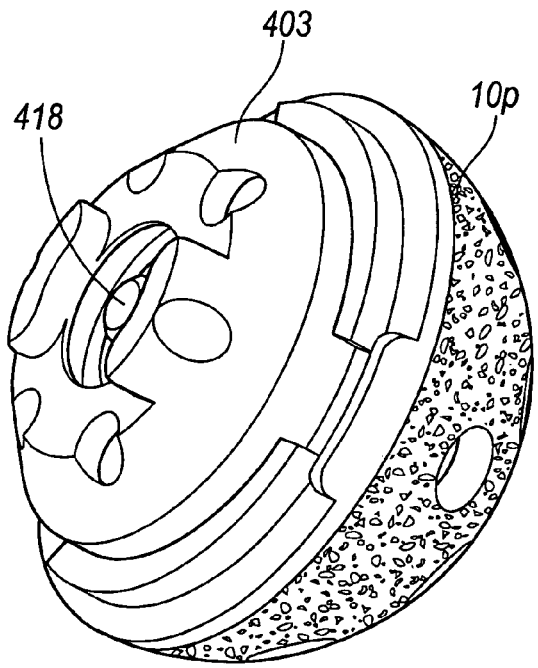
FIG. 38 illustrates the assembly tool of FIG. 37 shown mated with the solid metal rim.
Figure 39:
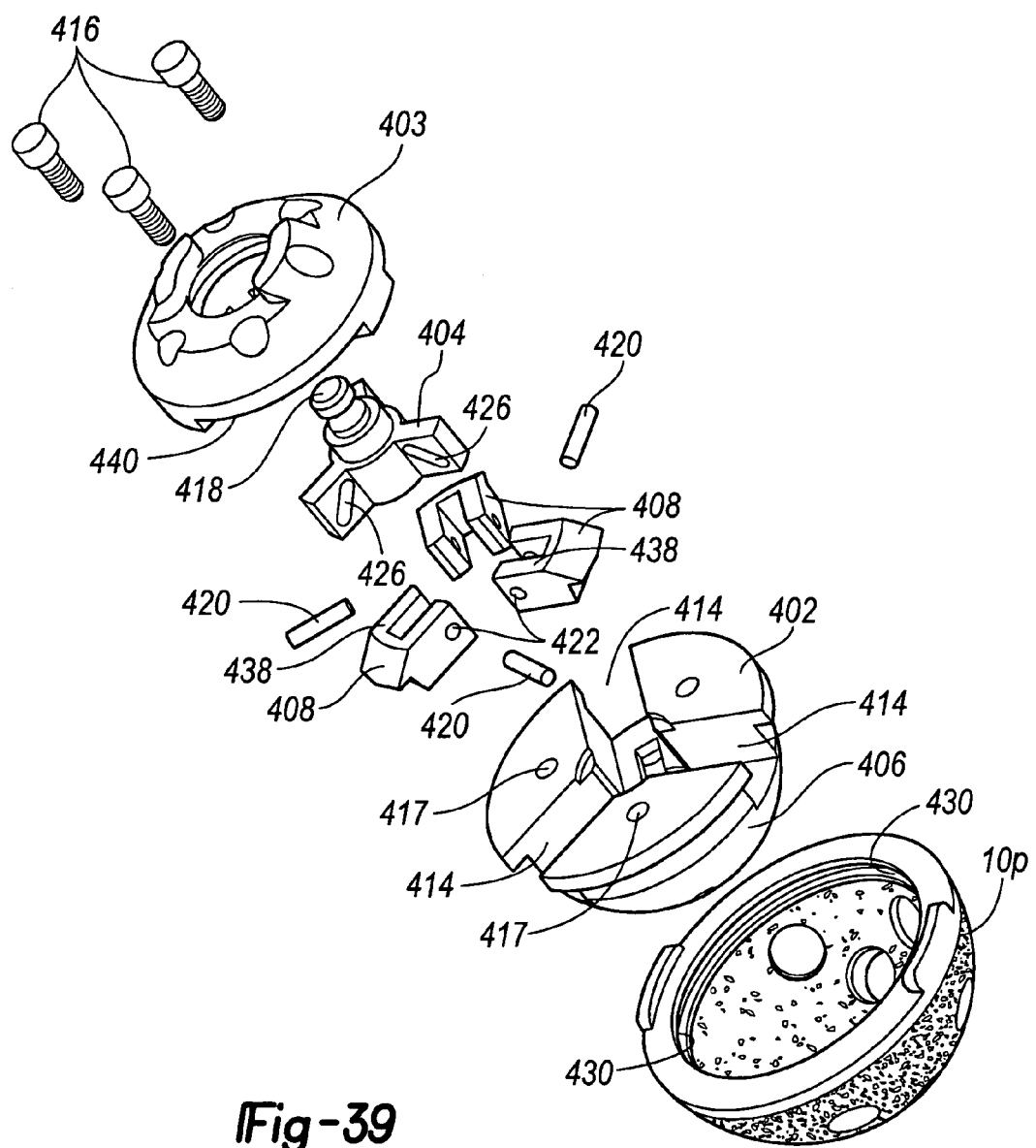
FIG. 39 is an exploded view of the assembly tool of FIG. 37 shown with the porous metal cup.
Figures 40, 41:
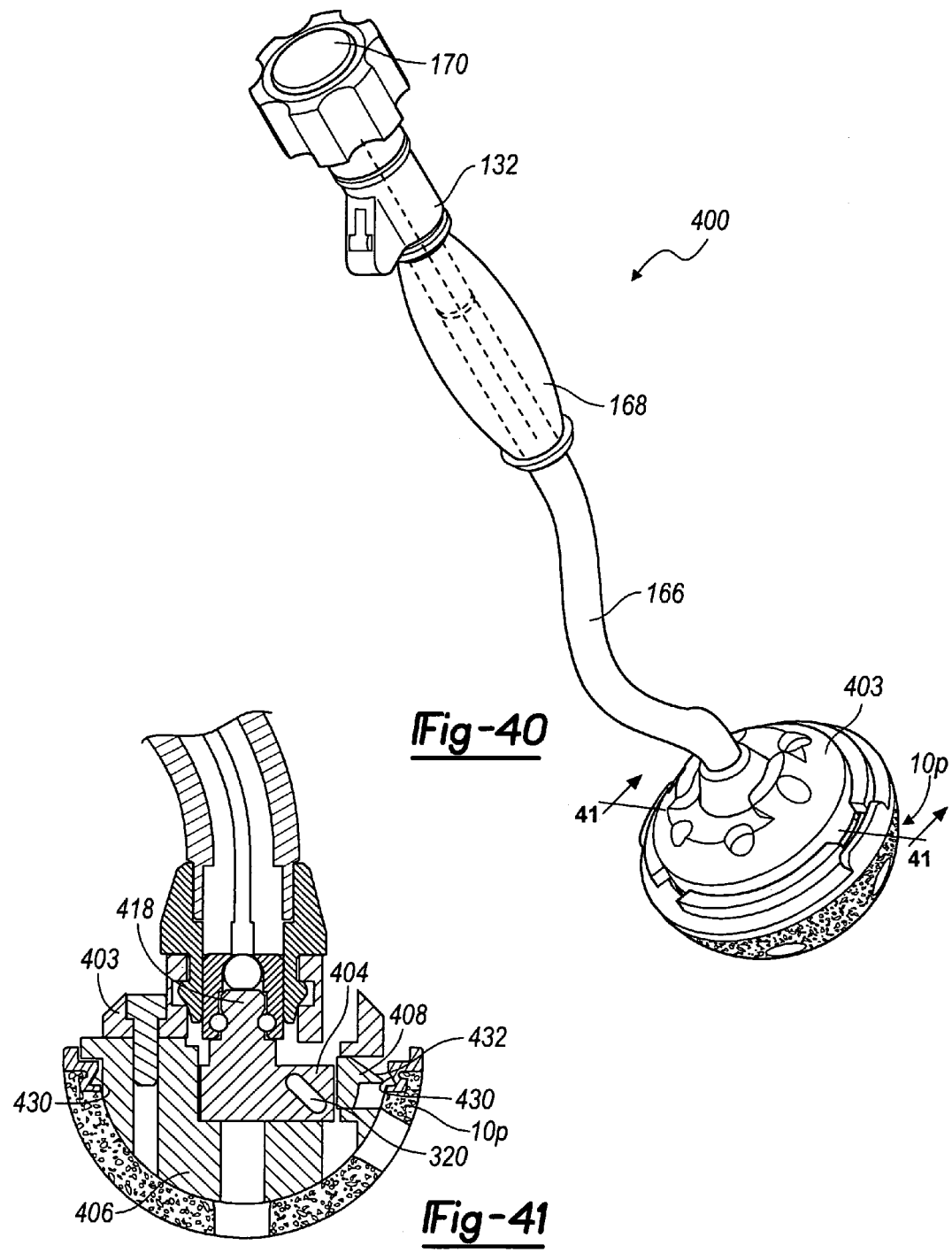
FIG. 40 is a perspective view of the assembly tool of FIG. 37 cooperating with an exemplary impaction handle.
FIG. 41 is a sectional view of FIG. 40 taken along line 41-41.

With reference now to FIGS. 27-31, another exemplary implantation tool 250 (FIG. 30) will be described. The implantation tool 250 generally includes the handle 132, a housing 256, a central member 260, a plate 261 and a pair of fingers 262. The housing 256 can include a cup portion 268 having a pair of passages 270 defined through a radial wall. A shaft portion 272 extends centrally from the central member 260 in a direction opposite the fingers 262. Pins 274 locate within respective bores 276 of the central member 260 and slots 278 of the fingers 262. The shaft portion 272 is adapted to cooperate with a driver such as disclosed above in relation to implantation tool 130. The fingers 262 nest in the passages 270 of the housing 256. The plate 261 may be adapted to locate within an annular space defined by the cup portion 268. The central member 260 is operable to move axially relative to the housing 256 along the passages 270 to facilitate a gripping action onto the solid ring 80. More specifically, the fingers 262 each define second tapered surfaces 280 (FIG. 29) adapted to mate with the first tapered surfaces 90 of the raised walls 86 on the solid ring 80 (FIG. 31).

An exemplary method of using the implantation tool 250 will now be described. At the outset, fingers 262 are aligned with the first tapered surfaces 90 of the raised walls 86 on the solid ring 80. Next, the knob 170 is rotated as viewed in FIG. 30 to pivot the fingers 262 outwardly about pins 274 to create tension between the first and second tapered surfaces 90, 280. Once the installation tool 250 has securely retained the acetabular cup 10*g*, the acetabular cup 10*g* may be located into a desired location on the patient (not shown). The impacting surface of the knob 170 may then be struck with an impacting tool until the acetabular cup 10*g* may be secured to the implantation site by any suitable methods. Once the acetabular cup 10*g* has been implanted to the desired position, the knob 170 may be rotated in an opposite direction to pivot the fingers 262 inwardly and away from engagement with the tapered surfaces 90. The implantation tool 250 may then be removed.

With reference now to FIGS. 32-35, another exemplary implantation tool 300 (FIG. 30) will be described. The implantation tool 300 generally includes the handle 132, a housing 302, a central member 304 and a pair of fingers 310. The housing 302 can include a cup portion 312 having a pair of passages 314 defined through a radial wall. A shaft portion (not show) extends centrally from the central member 304 in a direction opposite the fingers 310. Pins 318 locate within respective bores 220 of the central member 304 and 322 of the fingers 310. Similarly, pins 326 locate within respective bores 228 of the central member 304 and 330 of the housing 302. The shaft portion is adapted to cooperate with a driver such as disclosed above in relation to implantation tool 130. The fingers 310 nest in the passages 314 of the housing 302. The central member 304 is operable to move axially relative to the housing 302 along the passages 314 to facilitate a gripping action onto the solid ring 80. More specifically, the fingers 310 each define second tapered surfaces 332 (FIG. 34) adapted to mate with the first tapered surfaces 90 of the raised walls 86 on the solid ring 80 (FIG. 36).

An exemplary method of using the implantation tool 300 will now be described. At the outset, fingers 310 are aligned with the first tapered surfaces 90 of the raised walls 86 on the solid ring 80. Next, the knob 170 is rotated as viewed in FIG. 35 to pivot the fingers 310 outwardly about pins 322 to create tension between the first and second tapered surfaces 90, 332. Once the installation tool 300 has securely retained the acetabular cup 10*g*, the acetabular cup 10*g* may be located into a desired location on the patient (not shown). The impacting surface of the knob 170 may then be struck with an impacting tool until the acetabular cup 10*g* may be secured to the implantation site by any suitable methods. Once the acetabular cup 10*g* has been implanted to the desired position, the knob 170 may be rotated in an opposite direction to pivot the fingers 310 inwardly and away from engagement with the tapered surfaces 90. The implantation tool 300 may then be removed.

With reference now to FIGS. 37-41, another exemplary implantation tool 400 (FIG. 40) will be described. The implantation tool 400 generally includes the handle 132, a housing 402, a cap 403, a central member 404, a dome 406 (FIG. 39) and three fingers 408. The housing 402 defines three passage 414 defined through a radial wall. A shaft portion 418 extends centrally from the central member 404 in a direction opposite the fingers 408. Pins 420 locate within respective bores 422 of the central member 404 and angled slots 426 of the fingers 408. The shaft portion 418 is adapted to cooperate with a driver such as disclosed above in relation to implantation tool 130. The fingers 408 nest in the passages 414 of the housing 402. A series of fasteners 416 mate with threaded bores 417 in the housing 402 to retain the central member 404 and fingers 408 between the cap 403 and the housing 402.

The central member 404 is operable to move axially relative to the housing 402 along the passages 414 to facilitate a gripping action onto an inner radial tapered lip 430 of cup 10p. More specifically, the fingers 408 each define tapered surfaces 432 (FIG. 41) adapted to mate with the radial tapered lip 430 of the cup 10p. As the shaft portion 418 is urged upward (FIGS. 39 and 41), upper surfaces 438 of the fingers 408 slidably ride in a radially outward direction along a lower surface 440 of the cap 403. The pins 420 ride along the angled slots 426 causing the fingers 408 to move radially outwardly during upward movement of the central member 404.

An exemplary method of using the implantation tool 400 will now be described. At the outset, the fingers 408 are aligned with the radial tapered lip 430 of the cup 10p. Next, the knob 170 is rotated as viewed in FIG. 40 to slide the fingers 408 outwardly to create tension between the tapered surfaces 432 of the fingers 408 with the radial tapered lip 430 of the cup 10p. Once the installation tool 400 has securely retained the acetabular cup 10p, the acetabular cup 10p may be located into a desired location on the patient (not shown). The impacting surface of the knob 170 may then be struck with an impacting tool until the acetabular cup 10p may be secured to the implantation site by any suitable methods. Once the acetabular cup 10g has been implanted to the desired position, the knob 170 may be rotated in an opposite direction to pivot the fingers 408 inwardly and away from engagement with the radial tapered lip 430. The implantation tool 400 may then be removed.

While the invention has been described in the specification and illustrated in the drawings with reference to various embodiments, it will be understood by those skilled in the art that various changes may be made and equivalents may be substituted for elements thereof without departing from the scope of the invention as defined in the claims. Furthermore, the mixing and matching of features, elements and/or functions between various embodiments is expressly contemplated herein so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the teachings of the invention without departing from the essential scope thereof. Therefore, it is intended that the invention not be limited to the particular embodiment illustrated by the drawings and described in the specification as the best mode presently contemplated for carrying out this invention, but that the invention will include any embodiments falling within the foregoing description and the appended claims.

What is claimed is:

1. An orthopedic prosthesis comprising a hemispherical body that includes an open end defining a perimeter, said orthopedic prosthesis being formed of a porous metal shell, a non-porous rim defined at a radial edge of said porous metal shell and being metallurgically bonded to said porous metal shell such that said non-porous rim is non-removable from said porous metal shell, and a bearing liner separately formed from and insertable through said non-porous rim to a position against an inner bearing engaging surface of said porous metal shell, said porous metal shell defining continuous porous metal from said inner bearing engaging surface to an outer bone engaging surface, and defining a first annular pocket around said perimeter of said hemispherical body, said non-porous rim including a first annular collar formed around said perimeter that is received by said first annular pocket creating an overhanging interlock between said porous metal shell and said non-porous rim entirely around said perimeter, wherein said non-porous rim defines a second annular pocket around said perimeter that receives a second annular collar formed around said porous metal shell, wherein said non-porous rim includes at least one raised wall and an outer face that includes a planar surface, said at least one raised wall integrally formed with said non-porous rim and extending upright to a position laterally offset from said planar surface, said at least one raised wall adapted to mate with an attachment tool.

2. The orthopedic prosthesis of claim 1 wherein said at least one raised wall defines a tapered cross-section adapted to securably mate with a complementary tapered cross-section defined on said attachment tool.

3. The orthopedic prosthesis of claim 2 wherein said at least one raised wall comprises a pair of diametrically opposed raised walls integrally formed with said non-porous rim.

4. The orthopedic prosthesis of claim 3 wherein said pair of diametrically opposed raised walls do not extend inboard of an outermost diameter of said bearing engaging surface.

5. The orthopedic prosthesis of claim 3 wherein said non-porous rim does not extend inboard of an outermost diameter of said bearing engaging surface.

6. The orthopedic prosthesis of claim 4, further comprising:
   an annular ring selectively located within an annular groove formed on an
   inner surface of the non-porous rim, said annular ring capturing said bearing liner within said non-porous rim and said porous metal shell.

7. The orthopedic prosthesis of claim 6 wherein said annular ring is inboard of said diametrically opposed raised walls.

8. An orthopedic prosthesis for implantation into a bone of a patient, said orthopedic prosthesis comprising a hemispherical body that includes an open end defining a perimeter, said orthopedic prosthesis further comprising:
   a porous metal shell adapted to be affixed within the bone, said porous metal shell defining continuous porous metal from an inner bearing engaging surface to an outer bone engaging surface, said outer bone engaging surface adapted to receive bone ingrowth after the implantation;
   a non-porous rim defined at a radial edge of said porous metal shell and being metallurgically bonded to said porous metal shell by an application of high pressure that results in a bond between said non-porous rim and said porous metal shell such that said non-porous rim is non-removable from said porous metal shell; and
   a bearing liner separately formed from and insertable through said non-porous rim to a position against said inner bearing engaging surface of said porous metal shell;
   wherein said non-porous rim comprises:
      an interlocking structure defined by respective radially overlapping portions of porous metal shell and non-porous rim;
      at least one pair of raised walls extending proud from a planar surface defined on an outer face of said non-porous rim, wherein each raised wall of said at least one pair of raised walls defines a retaining feature formed thereon;
   wherein said interlocking structure is formed entirely around said perimeter of the orthopedic prosthesis and defines a first annular collar that projects radially outwardly from said non-porous rim and a first annular pocket formed in said porous metal shell, wherein said first annular collar nests within said first annular pocket, and wherein said interlocking structure further defines a second annular collar that projects radially inwardly from said porous metal shell and a second annular pocket formed in said non-porous rim, wherein said second annular collar nests within said second annular rim.

9. The orthopedic prosthesis of claim 8 wherein said at least one pair of raised walls extend to a position laterally offset from said planar surface.

10. The orthopedic prosthesis of claim 8 wherein each of said retaining features are positioned outboard of an outermost surface of said inner bearing engaging surface.

11. The orthopedic prosthesis of claim 8 wherein each of said retaining features comprise a tapered inner wall surface that slopes radially inwardly from said outer face of said non-porous rim.

12. The orthopedic prosthesis of claim 11 wherein each of said retaining features comprises two diametrically opposed retaining features.

13. The orthopedic prosthesis of claim 8, further comprising:
   an annular ring selectively located within an annular groove formed on an
   inner surface of the non-porous rim, said annular ring capturing said bearing liner within said non-porous rim and said porous metal shell.

14. The orthopedic prosthesis of claim 13 wherein said annular ring is inboard of said diametrically opposed raised walls in an installed position.

15. An orthopedic prosthesis for implantation into a bone of a patient, said orthopedic prosthesis comprising a hemispherical body that includes an open end defining a perimeter, said orthopedic prosthesis further comprising:
   a porous metal shell adapted to be affixed within the bone, said porous metal shell defining continuous porous metal from an inner bearing engaging surface to an outer bone engaging surface, said outer bearing engaging surface adapted to receive bone ingrowth after the implantation, said porous metal shell defining a first annular pocket formed thereon and a first annular collar that projects radially inwardly therefrom;
   a non-porous rim defined at a radial edge of said porous metal shell and being metallurgically bonded to said porous metal shell such that said non-porous rim is non-removable from said porous metal shell, said non-porous rim defining a second annular pocket formed thereon and a second annular collar that projects radially outwardly therefrom, wherein each of said first and second annular collars nest within each of said first and second annular pockets, respectively, creating an overhanging interlock between said porous metal shell and said non-porous rim entirely around said perimeter, said non-porous rim further comprising at least one pair of raised walls extending proud and raised above a planar surface defined on an outer face of said non-porous rim, wherein each raised wall of said at least one pair of raised walls defines a retaining feature formed at least in part by a wall surface tapering generally inwardly from said outer face of said non-porous rim; and
   a bearing liner separately formed from and insertable through said non-porous rim to a position against said inner bearing engaging surface of said porous metal shell.

16. The orthopedic prosthesis of claim 15 wherein said non-porous rim is formed entirely around said perimeter of the orthopedic prosthesis.

17. The orthopedic prosthesis of claim 15 wherein said porous metal shell defines a porosity gradient from said outer bone engaging surface to said inner bearing engaging surface and includes a combination of metal and pores having a ratio of between about 3:1 and about 8:1, respectively.

* * * * *

UNITED STATES PATENT AND TRADEMARK OFFICE
CERTIFICATE OF CORRECTION

PATENT NO. : 7,597,715 B2
APPLICATION NO. : 11/357868
DATED : October 6, 2009
INVENTOR(S) : Brown et al.

It is certified that error appears in the above-identified patent and that said Letters Patent is hereby corrected as shown below:

Column 6, line 14, insert --co-pending-- between in and application.

Column 7, line 37, delete "With" and insert --with--.

Column 9, line 31, delete "On" and replace with --10N--.

Column 7, line 50, delete "," after specifically.

Column 10, line 22, delete "show" and replace with --shown--.

Column 10, line 58, delete "passage" and replace with --passages--.

Signed and Sealed this

Twenty-second Day of December, 2009

David J. Kappos
*Director of the United States Patent and Trademark Office*